United States Patent [19]

Nagase et al.

[11] Patent Number: 5,417,983
[45] Date of Patent: May 23, 1995

[54] DRUG RELEASE CONTROLLING MATERIAL RESPONSIVE TO CHANGES IN TEMPERATURE

[75] Inventors: Yu Nagase; Takao Aoyagi, both of Sagamihara; Fusae Miyata, Tokyo, all of Japan

[73] Assignee: Sagami Chemical Research Center, Tokyo, Japan

[21] Appl. No.: 338,187

[22] Filed: Nov. 9, 1994

Related U.S. Application Data

[63] Continuation of Ser. No. 111,596, Aug. 25, 1993, abandoned, which is a continuation-in-part of Ser. No. 18,434, Feb. 16, 1993, abandoned.

[30] Foreign Application Priority Data

Feb. 19, 1992 [JP] Japan .................................. 4-69750
May 1, 1992 [JP] Japan ................................. 4-137614

[51] Int. Cl.$^6$ ............................................. A61K 9/00
[52] U.S. Cl. .................................... 424/487; 424/486; 424/473; 424/426; 424/489; 424/451; 424/409; 424/405; 524/559; 525/450; 525/921; 525/937; 526/292.4; 526/298; 526/320; 526/321; 528/354
[58] Field of Search ............... 424/487, 486, 473, 426; 524/559; 525/450, 921, 937; 526/320, 321, 292.4, 298; 528/354

[56] References Cited

U.S. PATENT DOCUMENTS

| | | | |
|---|---|---|---|
| 3,700,643 | 10/1972 | Smith et al. | |
| 4,540,809 | 9/1985 | Yokoshima et al. | 560/185 |
| 4,632,975 | 12/1986 | Cornell et al. | 528/354 |
| 4,692,336 | 9/1987 | Eckenhoff et al. | 424/468 |
| 5,053,228 | 10/1991 | Mori et al. | 424/486 |
| 5,139,790 | 8/1992 | Snipes | 424/435 |
| 5,330,768 | 7/1994 | Park et al. | 425/501 |

FOREIGN PATENT DOCUMENTS 1001149 8/1989 Belgium .

OTHER PUBLICATIONS

Die Makromolekulare Chemie, vol. 188, No. 10, pp. 2267–2275, Oct. 1987, Y. Gnanou, et al., "Synthesis of Poly(ε-Caprolactone) Macromonomers".

*Primary Examiner*—Mark Nagumo
*Attorney, Agent, or Firm*—Oblon, Spivak, McClelland, Maier & Neustadt

[57] ABSTRACT

The present invention related to a drug release controlling material responsive to changes in temperature comprising the polyester gel which is obtained by polymerization of a polyfunctional macromonomer represented by the general formula (I):

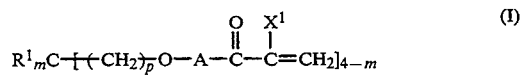

wherein $R^1$ represents a hydrogen atom or an alkyl group having from 1 to 6 carbon atoms, $X^1$ represents a hydrogen atom, a halogen atom, a cyano group, an alkyl group having from 1 to 6 carbon atoms or a phenyl group, A represents an aliphatic polyester chain, m is 0 or 1, and p, which may be the same or different in each branched chain, represents an integer of from 0 to 6, optionally with a polyethylene glycol derivative which contains polymerizable group(s) at the end(s). The drug release controlling material has an on-off control function of drug release responsive to changes in temperature depending upon the gel transition of the aliphatic polyester gel.

4 Claims, 13 Drawing Sheets

DRUG RELEASE CONTROLLING MATERIAL RESPONSIVE TO CHANGES IN TEMPERATURE

This application is a continuation of application Ser. No. 08/111,596, filed on Aug. 25, 1993, now abandoned, which is a continuation-in-part of Ser. No. 08/018,434, filed Feb. 16, 1993, now abandoned.

FIELD OF THE INVENTION

The present invention relates to a material for controlling a drug release responsive to changes in temperature, which comprises a polyester gel obtained by polymerization of a polyfunctional macromonomer which contains an aliphatic polyester chain as a main component and which contains 3 to 4 polymerizable substituents, optionally with a polyethylene glycol derivative which contains polymerizable group(s) at the end(s).

The polyester gel of the present invention makes it possible to control its thermal transition temperature by varying constituting components of the aliphatic polyester chain as a main component or the average polymerization degree thereof and, therefore, is useful as a material which can be used for an on-off control of drug release in any desired temperature range.

BACKGROUND OF THE INVENTION

Recently, a new technique for drug administration has recently been studied for the purpose of effectively-delivering a drug to a target portion thereby reducing possible side-effects, i.e., the drug delivery system (DDS). In particular, application of polymers which undergo changes in chemical structure, phase transition, and changes in shape and physical properties responsive to changes in surrounding conditions caused by, for example, a chemical substance, pH, temperature, electric or magnetic field, to a timing control of drug release is actively studied. By using a pharmaceutical preparation comprising such stimulus-responsive high molecular weight compounds, a drug delivery system having various functions can be obtained. For example, the pharmaceutical preparation per se notices a signal generated from physiological changes in the living body, determines an amount of the drug to be released depending upon the degree of physiological changes, and releases the drug or stops the drug release (on-off controlling function).

In particular, a temperature-sensitive drug releasing system using a polymeric material responsive to changes in temperature is capable of releasing the drug when required, for example, by releasing an antipyretic agent only when a patient has fever or external heat is applied, and is extensively studied as a practical DDS. The polymeric materials which have been proposed thus far and which respond to changes in temperature include a gel comprising poly-N-isopropylacrylamide as described in, for example, Okano et al., Hyomen (Surface Science), Vol. 10, p. 90, 1989, and J. Controlled Release, Vol. 11, p. 255, 1990; a gel comprising a copolymer of N-isopropylacrylamide and an alkyl methacrylate as described in, for example, Yoshida et al., Jinko Zoki (Artificial Organs), Vol. 19, p. 1243, 1990, and Drug Delivery System, Vol. 5, p. 279, 1990; an interpenetrating polymer network (IPN) gel comprising polyacrylic acid and polyacrylamide as described in, for example, Katono et al., J. Controlled Release, Vol. 16, p. 215, 1991; and a film comprising a porous film impregnated with liquid crystal molecules as described in, for example, Nozawa et al., J. Controlled Release, Vol. 15, p. 29, 1991. With these polymeric materials, the on-off control of the drug release responsive to changes in temperature is put into practical use by utilizing shrinking or swelling of gel depending upon changes in temperature, or by utilizing difference in permeability at a temperature just below or above the liquid crystal transition temperature.

However, the conventional polymers which respond to changes in temperature, that is, so-called temperature-responsive polymers, have various disadvantages such that they have poor mechanical strength, the temperature for the on-off control can not be optionally set, the polymers remain unchanged when used in the living body. In the case-of liquid crystal impregnated film, the liquid crystal molecule can not be fixed sufficiently and, therefore, the film is unstable in repeated use. For the reasons described above, the conventional temperature-responsive polymers have not yet been put into practical use. In particular, since the on-off control of the drug release is mostly performed in the living body, it is highly desirable to use a material which can be degraded and absorbed in the living body or under natural environmental conditions. However, it has not been proposed to use the biodegradable polymer as a temperature-responsive polymer.

As a result of extensive studies, the present inventors have found a novel temperature-responsive polymer which is degraded and absorbed in the living body or under natural environmental conditions after use and also which is free from problems associated with the conventional materials such that the materials have poor mechanical strength and are difficult to optionally set the temperature at which the on-off control is performed. The novel polymer can be produced by using a polymer which mainly comprises aliphatic polyesters such as polylactide, polyglycollide, poly-γ-butyrolactone, poly-ε-caprolactone, poly-β-hydroxybutyric acid and poly-β-hydroxyvaleric acid which are known as biodegradable polymers as described in Kobunshi Shinsozai Binran (Bulletin of Polymeric New Materials), edited by the Society of Polymer Science, Japan, 1989, pp. 322–347, and completed the present invention.

SUMMARY OF THE INVENTION

The object of the present invention is therefore to provide a novel temperature-responsive polymeric material mainly comprising a biodegradable polymeric material having mechanical properties suitable for use in various utilities, in particular, a high tensile elongation, by forming a three-dimensional crosslinked material, i.e., gel, which comprises, as a main component, a polymeric chain composed of an aliphatic polyester such as polylactide, polyglycollide, polylactones and poly-β-hydroxyalkanoate or copolymers thereof.

The polyester gel possesses mechanical properties suitable to various utilities, in particular, as a biodegradable polymeric material having a high tensile elongation. The gel can be provided with any desirable mechanical properties and gel transition temperatures by varying constituting components of the aliphatic polyester chain as a main component and average polymerization degree of the gel. The drug release controlling material has an on-off control function of drug release responsive to changes in temperature depending upon the gel transition of the aliphatic polyester gel, i.e., just below or above the transition temperature of the gel.

DETAILED DESCRIPTION OF THE INVENTION

Figure 1:
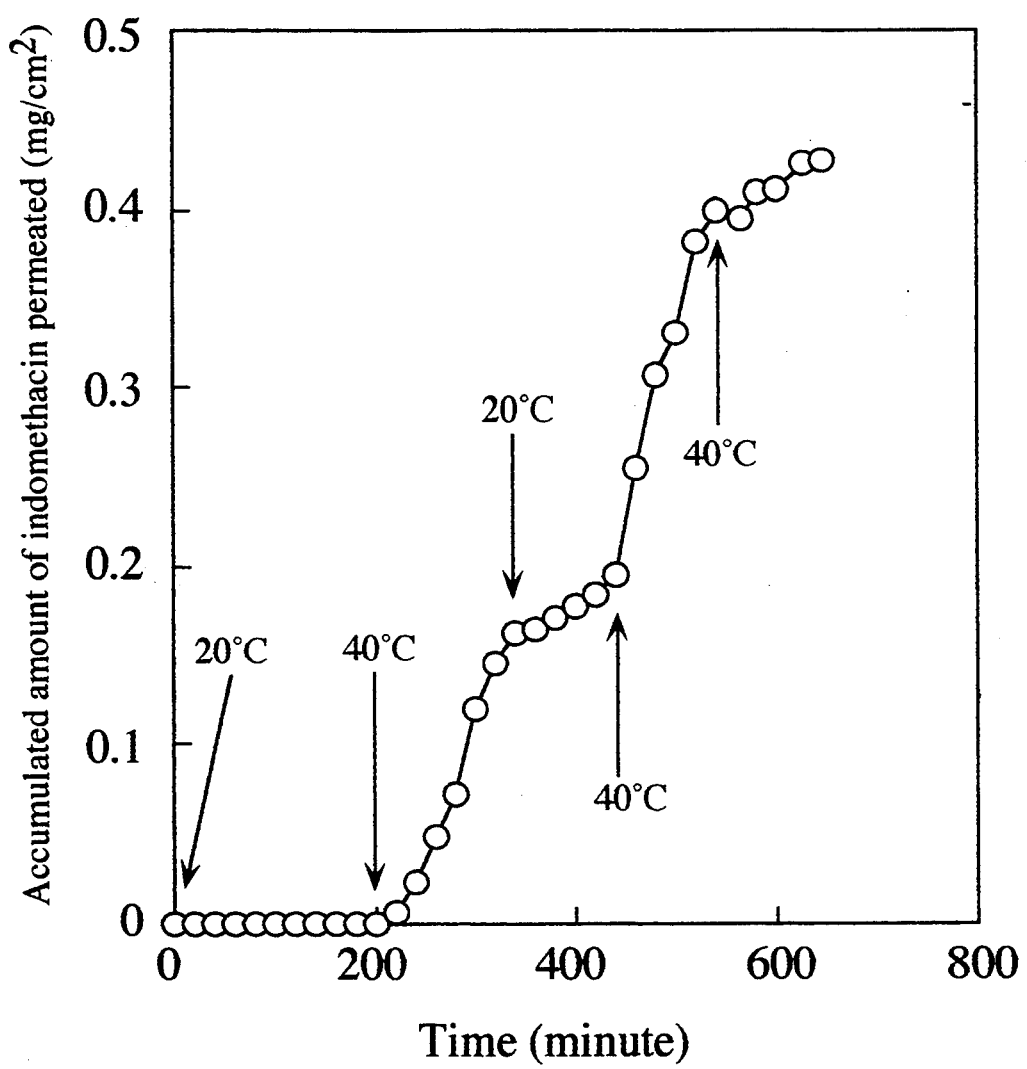
FIG. 1 is a graph showing a test result of Example 4 on permeation of indomethacin using a gel membrane produced in Referential Example 38.

The drug release controlling material responsive to changes in temperature comprises a polyester gel obtained by polymerization of a polyfunctional macromonomer represented by the general formula (I):

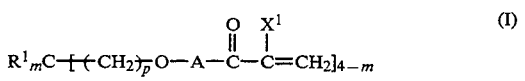

wherein $R^1$ represents a hydrogen atom or an alkyl group having from 1 to 6 carbon atoms, $X^1$ represents a hydrogen atom, a halogen atom, a cyano group, an alkyl group having from 1 to 6 carbon atoms or a phenyl group, A represents an aliphatic polyester chain, m is 0 or 1, and p, which may be the same or different in each branched chain, represents an integer of from 0 to 6.

The aliphatic chain represented by A in the above general formula (I) is, preferably, composed of a repeating unit represented by the general formula (II):

wherein $R^2$ which may be the same or different in each repeating unit, represents a hydrogen atom, a methyl group or an ethyl group, and q, which may be the same or different in each repeating unit, represents an integer of from 0 to 6, and is characterized by having an average polymerization degree in the range of from 5 to 500.

The present invention also includes a drug release controlling material responsive to changes in temperature comprises a polyester gel obtained by polymerization of a polyfunctional macromonomer represented by the general formula (I):

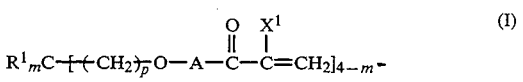

wherein $R^1$ represents a hydrogen atom or an alkyl group having from 1 to 6 carbon atoms, X represents a hydrogen atom, a halogen atom, a cyano group, an alkyl group having from 1 to 6 carbon atoms or a phenyl group, A represents an aliphatic polyester chain, m is 0 or 1, and p, which may be the same or different in each branched chain, represents an integer of from 0 to 6, and a polyethylene glycol derivative represented by the general formula (III):

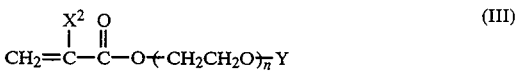

wherein $X^2$ represents a hydrogen atom, a halogen atom, a cyano group, an alkyl group having from 1 to 6 carbon atoms or a phenyl group, Y represents a hydrogen atom, an alkyl group having from 1 to 6 carbon atoms or a group represented by —C(=O)C($X^2$)=CH$_2$, n represents an integer of from 5 to 50, after mixing them in a ratio of the compound represented by the formula (I)/the polyethylene glycol derivative ranging from 99/1 to 70/30 by weight.

The polyester polyfunctional macromonomer represented by the above general formula (I) according to the present invention can be easily prepared by, for example, ring-opening polymerization of a cyclic ester compound represented by the general formula (IV):

wherein $R^2$ is as defined above, or the general formula (V):

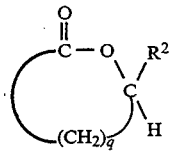

wherein $R^2$ and q are as defined above, or a mixture thereof, in the presence of a triol or tetraol compound represented by the general formula (VI):

wherein $R^1$, m and p are as defined above, to obtain a precursor represented by the general formula (VII):

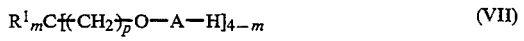

wherein $R^1$ A, m and p are as defined above, and reacting the resulting precursor with an acid chloride represented by the general formula (VIII):

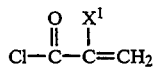

wherein $X^1$ is as defined above.

Examples of the triol or tetraol compound represented by the general formula (VI) used above include glycerin, 1,1,1-tri(hydroxymethyl) ethane, 1,1,1-tri (hydroxymethyl)propane, 1,1,1-tri(hydroxymethyl)butane, 1,1,1-tri(hydroxymethyl)pentane, 1,1,1-tri(hydroxymethyl) hexane, 1, 1,1-tri (hydroxymethyl) heptane, pentaerythritol, 1,3,5-tri (hydroxymethyl) pentane, 1,3,3,5-tetra(hydroxymethyl)pentane, 1,2, 6-trihydroxyhexane and 1,2,2,6-tetrahydroxyhexane.

Examples of the cyclic ester compound represented by the general formula (IV) or (V) include glycollide, D,L-lactide, L-lactide, D-lactide, β-propiolactone, β-butyrolactone, γ-butyrolactone, β-valerolactone, γ-valerolactone, δ-valerolactone, γ-caprolactone, δ-caprolactone and ε-caprolactone. These cyclic ester compounds can be used singly or as a mixture thereof, and by heating the cyclic ester compound at a temperature of from 50° C. to 200 ° C., preferably from 100 ° C. to 200 ° C., in the presence of the triol or tetraol compound represented by the general formula (VI), the ring-opening polymerization proceeds easily to obtain the precursor represented by the general formula (VIII) above. When the ring-opening polymerization is performed using a lactide, a catalyst is preferably used. Examples of the catalyst which can be used include tin type catalysts, such as tin 2-ethylhexanoate, tributyltin acetate, tributyltin chloride, methoxytributyltin and t-butoxytributyltin; antimony type catalysts such as antimony trioxide, antimony trichloride, antimony pentachloride and antimony trifluoride; and zinc type catalysts such as zinc powder, zinc oxide, zinc acetate, zinc chloride and zinc fluoride.

Examples of the acid chloride represented by the general formula (VIII) which can be used for producing the polyester polyfunctional macromonomer represented by the general formula (I) of the present invention from the thus-produced precursor represented by the general formula (VII) above include acryloyl chloride, α-chloroacryloyl chloride, α-cyanoacryloyl chloride, methacryloyl chloride, α-butylacryloyl chloride and α-phenylacryloyl chloride. The reaction between the precursor of the general formula (VII) and the acid chloride of the general formula (VIII) is preferably carried out in an organic solvent. Examples of preferred organic solvents include tetrahydrofuran, benzene, toluene, chloroform, carbon tetrachloride, N,N-dimethylformamide, dimethyl sulfoxide, and the like. Since hydrogen chloride is generated during the reaction, the reaction is preferably conducted in the presence of an organic base such as triethylamine, N,N-dimethylaniline and pyridine as a scavenger of hydrogen chloride.

The polyethylene glycol derivative represented by the formula (III) is partly commercially available, and may be also easily prepared by reacting a commercially available polyethylene glycol having hydroxyl group(s) at the one or both ends with an acid chloride represented by the formula (IX):

wherein $X^2$ represents a hydrogen atom, a halogen atom, a cyano group, an alkyl group having from 1 to 6 carbon atoms or a phenyl group.

In producing the polyester gel of the present invention by polymerization of the polyfunctional macromonomer of the general formula (I) obtained as above, a conventional addition polymerization method such as a radical polymerization, an anionic polymerization and a cationic polymerization can be used, with the radical polymerization being the most advantageous method.

The polyester gel obtained by polymerization of a polyfunctional macromonomer represented by the general formula (I) and a polyethylene glycol derivative represented by the general formula (III) can also be produced similarly using the macromonomer and polyethylene glycol derivative as the starting monomers. The weight ratio of the macromonomer represented by the formula (I) to the derivative represented by the formula (III) ranges from 99/1 to 70/30, preferably from 95/5 to 80/20. The increase of the ratio of the former monomer reduces the permeation of a drug through the resulting gel, and on-off control relative to change in temperature becomes difficult when the ratio of the former monomer is too small.

The radical polymerization can be carried out by a conventional procedure such as bulk polymerization, solution polymerization and emulsion polymerization method. Also, the radical polymerization can be initiated by merely heating, radiation with visible light or ultraviolet rays or by adding a radical polymerization initiator. Examples of the radical polymerization initiator which are preferably used in the reaction include organic peroxides such as dilauroyl peroxide, di-t-butyl peroxide, benzoyl peroxide, t-butylhydroxy peroxide and cumene hydroperoxide, or azo compounds such as α,α'-azobisisobutyronitrile, and azobiscyclohexanecarbonitrile. When the polymerization is initiated by radiation with visible light or ultraviolet rays, the polymerization is preferably initiated in the presence of conventional photo-polymerization initiator and a sensitizer. Examples of the photopolymerization initiator which can be used include benzoin, benzophenone, acetophenon, benzil, p,p'-dimethoxybenzil, camphorquinone, p,p'-dichlorobenzil, camphorquinone, α-naphthyl, acenaphthene, thioxanthone, 2-chlorothioxanthone, 2-methylthioxanthone and 2,4-diethoxythioxanthone, trimethylbenzoyldiphenylphosphine oxide. Examples of the sensitizer which can be preferably used include n-butylamine, triethylamine, dimethylaminoethyl methacrylate, N,N-dimethylaniline, N,N-dimethyltoluidine, triethyl-n-butylphosphine, and isoamyl 4-dimethylaminobenzoate. Examples of the organic solvent which can be used include benzene, toluene, xylene, chlorobenzene, tetrahydrofuran, chloroform, methyl ethyl ketone, fluorobenzene, methanol, ethanol, n-propanol, isopropanol, N,N-dimethylformamide and N,N-dimethylacetamide, but the solvent is not limited thereto. The polymerization reaction proceeds smoothly at a temperature in the range of from room temperature to 100° C. The polymerization reaction can be carried out in a usual reaction vessel under stirring, but it can also be conducted by pouring a starting macromonomer and necessary reagents such as a solvent and a polymerization initiator into a space between glass plates or into a mold. Accordingly, the gel may be formed in any desired shape such as film or membrane, plate, rod, sphere, tube and pellet during the polymerization, and can be further subjected to a secondary processing such as stretching and spinning.

As shown in the test examples described hereinafter, the thus-obtained polyester gel which can be used in the present invention can be provided with different mechanical properties such as tensile modulus, tensile strength and elongation percentage by changing the component in the repeating unit of the aliphatic polyester chain represented by A in the polyfunctional macromonomer or the average polymerization degree, and further, the gel transition temperature can be optionally controlled. In particular, when it is desired to conduct the on-off control depending on the drug-releasing temperature at a temperature in the living body, i.e., about from 30° to about 40° C. the component in the repeating unit of the aliphatic polyester chain represented by A in the polyfunctional macromonomer of the general formula (I) is desirably a component containing polylactone, and the average polymerization degree thereof is preferably in the range of from 5 to 100. Further, since the gel can be fabricated into any desired shapes during the polymerization of the macromonomer starting material as described above, it is possible to form a desired shape suitable to the intended utility of the material such as films, membranes, plates, rods, sphere, tubes, needles, threads or microcapsules. Thus, the polyester gel according to the present invention can be used for wide variety of utilities, for example, hydrolyzable or biodegradable plastics, rubbers or fibers, absorbable suture threads, or matrix for sustained release preparations of drugs such as medicines, agricultural agents or microcidal agents.

In preparing preparations comprising the drug release controlling material according to the present invention, the drug can be incorporated into the gel by mixing the drug with the polyfunctional macromonomer during the polymerization of the macromonomer, or by impregnating the gel with the drug, or sealing the drug into the gel which has been shaped in the form of films, membranes, tubes, capsules or the like.

The drugs used in the DDS which is responsive to changes in temperature by using the drug release controlling material of the present invention can be any type of drugs for human or animals. Examples of drugs include anti-inflammatory analgesic agent such as acetaminophenone, acetyl salicycloyl (aspirin), methyl salicylate, choline saticylate, glycol salicylate, 1-menthol, camphor, mefenamic acid, flufenamic acid, antipyrine, indomethacin, diclofenac, alclofenac, ibuprofen, ketoprofen, naproxen, pranoprofen, fenoprofen, fenprofen, flurbiprofen, indoprofen, fentiazac, tolmetin, suprofen, benzadac, bufexamac, piroxicam, phenylbutazone, oxyphenbutazone, clofezone, pentazocine and mepirizole; steroid type anti-inflammatory agents such as hydrocortisone, predonisolone, dexamethasone, triamcinolone acetonide, fluocinolone acetonide and fludorocortisone acetate; antihistamic of antiallergic agents such as chlorpheniramine, glycyrrhizic acid, diphenhydramine and periactin; local anesthetic agents such as benzocaine, procaine, dibucaine and lidocaine; antimicrobial agents such as tetracyclines, e.g., chlortetracycline, penicillins, e.g., ampicillin, cephalosporines, e.g., cefalotin, aminoglycosides, e.g., kanamycin, macrolides, e.g., erythromycin, chloramphenicol, iodine compounds, nitrofurantoin, nystatin, amphotericin, fradiomycin, sulfonamides, pyrrolnitrin, clotrimazole and nitrofurazone; antihypertensive agents such as clonidine, α-methyldopa, reserpine, syrosingopine, rescinnamine, cinnarizine, hydrazine and prazosin; hypotensive diuretic agents such as theophylline, trichlormethiaide, furosemide, tribamide, methylclothiazide, penflutizide, hydrothiazide, spironolactone and metolazone; cardiotonic agents such as digitalis, ubidecarenone and dopamin; coronary vasodilators such as nitroglycerin, isosorbitol dinitrate, erythritol tetranitrate, pentaerythritol tetranitrate, dipyridamole, dilazep, trapidil and trimetazidine; vasoconstrictors such as dihydroergotamine and dihydroergotoxine; β-blockers or antiarrhythmic agents such as pindolol and propranolol; calcium antagonists such as diltiazem, nifedipine, nicardipine, verapamil, bencyclan and dilazep; antiepileptic agents such as nitrazepam, meprobamate and phenytoin; antivertigo agents such as isoprenaline, betahistine and scopolamine; psycholeptics such as diazepam, lorazepam, flunitrazepam and fluphenazine; hypnotic sedatives such as phenobarbital, amobarbital and cyclobarbital; muscle relaxants such as triperizone, baclofen, tantrolene sodium and cyclopenzaprine; agents for autonomic nerves such as atropine and levodopa; agents for respiratory organs such as codeine, ephedrine, isoproterenol, dextromethorphan, oleciprenatorin, ipratropium bromide and cromoglicic acid; hormones and antihormone agents such as corticotropin, oxytocin, vasopressin, testosterone, progesterone and estradiol; salivary gland hormones, thyroid hormones, adorenal hormones, kallikrein, insulin and oxendolone; vitamins A, B, C, D, E, K and their derivatives, calciferols and mecobalamin; antitumor agents such as 5-fluorouracil and derivatives thereof, adriamycin, krestin, picibanil, ancitabine and cytarabine; enzymes such as urokinase; herb medicines or herb extracts such glycyrrhiza, aloes and allantoin, aldioxa and alcloxa; and others such as prostaglandins, antidiabetic agents. These drugs may be used alone or in a combination of two or more drugs. The DDS using the drug release controlling material according to the present invention which is responsive to changes in the temperature is not limited to the use of the above-described drugs and can also be applied to agricultural agents such as insecticides, herbicides and fertilizers according to the intended utility. Thus, the term "drug" in the present specification and claims includes not only the drugs for medication but also any physiologically active agents such as the agricultural agents and any test or marker agents. Accordingly, the use of the material according to the present invention for controlling the release of the agricultural agents, of course, falls within the scope of the present invention.

EXAMPLES

The present invention is further illustrated by the following Referential Examples, Examples, and test examples, but they are not construed as limiting the present invention. In the following $^1$H-NMR spectral data, the symbol "H" stands for a proton assigned to its chemical shift.

REFERENTIAL EXAMPLES 1 to 4 hexane/diethyl ether/methanol (18/1/1 by volume) to obtain a trifunctional macromonomer having a structure represented by the chemical formula (2) above as a white powder. An amount of the product, a yield (%), an average polymerization degree determined from a peak area ratio of $^1$H-NMR spectrum, and a weight-average molecular weight determined based on the polystyrene standards by GPC are shown in Table 1 below.

$^1$H-NMR, δ(CDCl$_3$, ppm); 0.88 (t, C"H"$_3$CH$_2$—), 1.58 (m, —CH$_2$(C"H"$_2$)$_3$CH$_2$O—, CH$_3$C"H"$_2$—), 1.90 (s, —C(C"H"$_3$)=CH$_2$), 2.31 (t, —COC"H"$_2$—), 4.06 (t, —C"H"$_2$O —), 5.58 (d, —C (CH$_3$)=C"H"$_2$), 6.12 (d, —C(CH$_3$)=C"H"$_2$). IR (cm$^{-1}$); 2940, 2870, 1730 (C=O), 1640 (C=C), 1470, 1420, 1370, 1300, 1240, 1190, 1110, 1050, 960, 840, 730.

TABLE 1

| Ref. Example No. | Amount of THP g (mmol) | Amount of CL g (mmol) | Yield, g (% yield) | Average Polymerization Degree | Weight-average Molecular Weight |
|---|---|---|---|---|---|
| 1 | 12.1 (90.2) | 103 (902) | 83.2 (72.3) | 3.0 | 2.83 × 10$^3$ |
| 2 | 2.00 (14.9) | 34.0 (298) | 31.9 (88.6) | 6.1 | 7.49 × 10$^3$ |
| 3 | 2.42 (18.0) | 82.4 (722) | 82.7 (97.5) | 13.2 | 1.20 × 10$^4$ |
| 4 | 0.605 (4.51) | 41.2 (361) | 38.2 (91.5) | 25.5 | 2.20 × 10$^4$ |

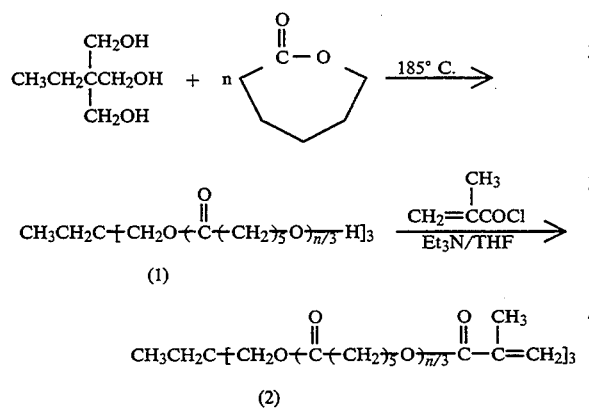

REFERENTIAL EXAMPLES 5 TO 9

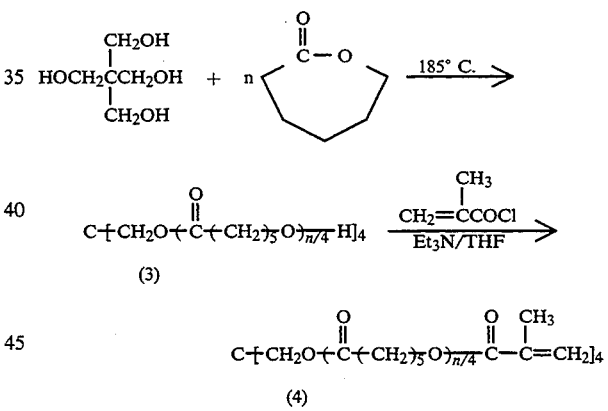

1, 1, 1-Tri (hydroxymethyl) propane (hereinafter abbreviated as THP) and ε-caprolactone (hereinafter abbreviated as CL) in amounts shown in Table 1 below were mixed and heated at 185° C. for 3 days under stirring. The resulting reaction mixture was dissolved in acetone and reprecipitated in an excess amount of a mixed solvent of hexane/diethyl ether (1/1 by Volume) to obtain a precursor comprising poly-ε-caprolactone represented by the above chemical formula (1) as a while powder.

$^1$H-NMR, δ(CDCl$_3$, ppm); 0.88 (t, C"H"$_3$CH$_2$—), 1.58 (m, —CH$_2$(C"H"$_2$)$_3$CH$_2$)—, CH$_3$C"H"$_2$—), 2.31 (t, —COC"H"$_2$—), 4.06 (t, —C"H"$_2$O—). IR (cm$^{-1}$); 3520 (—OH), 2940, 2870, 1730 (C=O), 1470, 1420, 1370, 1300, 1240, 1190, 1110, 1050, 960, 730.

The resulting precursor was dissolved in tetrahydrofuran, and about 7.5 molar equivalent of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of Pentaerythritol (hereinafter abbreviated as PET) and CL in amounts shown in Table 2 below were mixed, and the mixture was heated at 185° C. for 3 days under stirring. The resulting reaction mixture was dissolved in acetone and reprecipitated in an excess amount of a mixed solvent of hexane/diethyl ether (1/1 by volume) to obtain a precursor comprising poly-ε-caprolactone represented by the chemical formula (3) above.

$^1$H-NMR, δ(CDCl$_3$, ppm); 1.58 (m, —CH$_2$(C"H"$_2$)$_3$CH$_2$O—), 2.31 (t, —COC"H"$_2$—), 4.06 (t, —C"H"$_2$O—). IR (cm$^{-1}$); 3520 (—OH), 2940, 2870, 1730 (C=O), 1470, 1420, 1370, 1300, 1240, 1190, 1110, 1050, 960, 730.

The resulting precursor was dissolved in tetrahydrofuran, and about 7.5 molar equivant of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (4) above as a white powder. An amount of the product, a yield (%), an average polymerization degree determined from a peak area ratio of $^1$H-NMR spectrum, and a weight-average molecular weight determined based on the polystyrene standards by GPC are shown in Table 2 below.

$^1$H-NMR, δ(CDCl$_3$, ppm); 1.58 (m, —CH$_2$(C″H″$_2$)$_3$CH$_2$O—), 1.90 (s, —C(C″H″$_3$)=CH$_2$), 2.31 (t, —COC″H″$_2$—), 4.06 (t, —C″H″$_2$O—), 5.58 (d,—C (CH$_3$)=C″H″$_2$), 6.12 (d, —C (CH$_3$)=C″H″$_2$). IR (cm$^{-1}$); 2940, 2870, 1730 (C=O), 1640(C=C), 1470, 1420, 1370, 1300, 1240, 1190, 1110, 1050, 960, 840, 730.

Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a trifunctional macromonomer having a structure represented by the chemical formula (6) above as a white powder. The yield was 6.68 g (65.3% yield). Also, the average polymerization degree calculated from the peak area ratio of $^1$H-NMR spectrum was 12.5, and the weight-average molecular weight determined based on the polystyrene standards by GPC was $1.24 \times 10^4$.

$^1$H-NMR, δ(CDCl$^3$, ppm); 0.89 (t, C″H″$_3$CH$_2$—), 1.54 (m, —CH(C″H″$_3$)O—), 1.60 (m, CH$_3$C″H″$_2$—), 1.90 (s, —C(C″H″$_3$)=CH$_2$), 4.05 (t, —C″H″$_2$O—), 5.16 (q, C″H″(CH$_3$)O—), 5.58 (d, —C(CH$_3$)=C″H″$_2$), 6.12

TABLE 2

| Ref. Example No. | Amount of PET g (mmol) | Amount of CL g (mmol) | Yield, g (% yield) | Average Polymerization Degree | Weight-average Molecular Weight |
|---|---|---|---|---|---|
| 5 | 12.3 (90.3) | 103 (902) | 80.9 (78.6) | 2.3 | $2.78 \times 10^3$ |
| 6 | 2.46 (18.1) | 41.2 (361) | 34.1 (78.2) | 4.7 | $6.90 \times 10^3$ |
| 7 | 2.46 (18.1) | 82.4 (722) | 83.2 (98.1) | 9.5 | $1.02 \times 10^4$ |
| 8 | 1.23 (9.03) | 82.4 (722) | 74.2 (88.7) | 19.1 | $2.05 \times 10^4$ |
| 9 | 0.398 (2.92) | 40.0 (350) | 35.9 (88.7) | 28.5 | $4.87 \times 10^4$ |

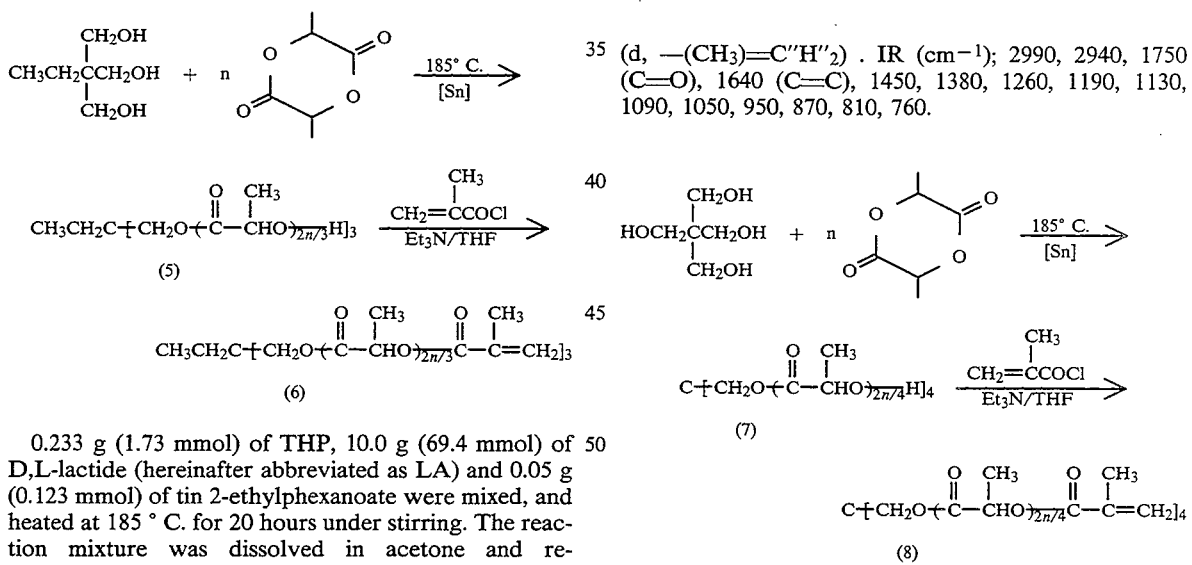

(d, —(CH$_3$)=C″H″$_2$) . IR (cm$^{-1}$); 2990, 2940, 1750 (C=O), 1640 (C=C), 1450, 1380, 1260, 1190, 1130, 1090, 1050, 950, 870, 810, 760.

0.233 g (1.73 mmol) of THP, 10.0 g (69.4 mmol) of D,L-lactide (hereinafter abbreviated as LA) and 0.05 g (0.123 mmol) of tin 2-ethylhexanoate were mixed, and heated at 185 ° C. for 20 hours under stirring. The reaction mixture was dissolved in acetone and reprecipitated in an excess amount of a mixed solvent of hexane/diethyl ether/methanol (1/1/0.05 by volume) to obtain a precursor comprising polylactide represented by the chemical formula (5) above as a white powder.

$^1$H-NMR, δ(CDCl$_3$, ppm); 0.89 (t, C″H″$_3$CH$_2$—), 1.54 (m, —CH(C″H″$_3$)O—), 1.60 (m, CH$_3$C″H″$_2$—), 4.05 (t, —C″H″$_2$O—), 5.16 (q, C″H″(CH$_3$)O—). IR (cm$^{-1}$); 3550 (—OH), 2990, 2940, 1750 (C=O), 1450, 1380, 1260, 1190, 1130, 1090, 1050, 950, 870, 760.

The resulting precursor was dissolved in tetrahydrofuran, and about 7.5 molar equivalent of methacryloyl chloride and triethylamine were added to the solution, followed by stirring for hours at room temperature.

0.235 g (1.73 mmol) of PET, 10.0 g (69.4 mmol) of LA and 0.05 g (0.123 mmol) of tin 2-ethylhexanoate were mixed and heated at 185° C. for 24 hours under stirring. The resulting reaction mixture was dissolved in acetone and reprecipitated in an excess amount of a mixed solvent of hexane/diethyl ether/methanol (1/1/0.05 by volume) to obtain a precursor comprising a polylactide represented by the chemical formula (7) above as a white powder.

$^1$H-NMR, δ(CDCl$_3$, ppm); 1.54 (m, —CH(C″H″$_3$)O—), 4.05 (t, —C″H″$_2$O—), 5.16 (q, C″H″(CH$_3$)O—) . IR (cm$^{-1}$); 3550 (—OH), 2990, 2940, 1750 (C=O), 1450, 1380, 1260, 1190, 1130, 1090, 1050, 950, 870, 760.

The resulting precursor was dissolved in tetrahydrofuran, and about 10 molar equivalent of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (8) above as a white powder. The yield was 7.87 g (76.9% yield). Also, the average polymerization degree calculated from the peak area ratio of $^1$H-NMR spectrum was 9.4, and the weight-average molecular weight determined based on the polystyrene standards by GPC was $1.16 \times 10^4$.

$^1$H-NMR, δ(CDCl$_3$, ppm); 1.54 (m, —CH(C″H″$_3$)O—), 1.90 (s, —C(C″H″$_3$)=CH$_2$), 4.05 (t, —C″H′$_2$O—), 5.16 (q, C″H″(CH$_3$)O—), 5.58 (d, —C(CH$_3$)=C″H″$_2$), 6.12 (d, —C (CH$_3$)=C″H″$_2$) . IR (cm$^{-1}$); 2990, 2940, 1750 (C=O), 1640 (C=C), 1450, 1380, 1260, 1190, 1130, 1090, 1050, 950, 870, 810, 760.

Each of the resulting precursors was dissolved in tetrahydrofuran, and about 10 molar equivalent of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (10) above as a white powder. An amount of the product, a yield (%), an average polymerization degree determined from a peak area ratio of $^1$H-NMR spectrum, and a weight-average molecular weight determined based on the polystyrene standards by GPC are shown in Table 3 below.

$^1$H-NMR, δ(CDCl$_3$, ppm); 1.54 (m, —CH(C″H″$_3$)O—), 1.90 (s, —C(C″H″$_3$)=CH$_2$), 4.05 (t, —C″H′$_2$O—), 5.16 (q, C″H″(CH$_3$)O—), 5.58 (d, —C(CH$_3$)=C″H″$_2$), 6.12 (d, —C(CH$_3$)=C″H″$_2$). IR (cm$^{-1}$); 2990, 2940, 1760 (C=O), 1720, 1640 (C=C), 1450, 1380, 1360, 1270, 1190, 1130, 1090, 1050, 870, 810, 760.

TABLE 3

| Ref. Example No. | Amount of PET g (mmol) | Amount of LLA g (mmol) | Yield, g (% yield) | Average Polymerization Degree | Weight-average Molecular Weight |
| --- | --- | --- | --- | --- | --- |
| 12 | 1.89 (13.8) | 20.0 (138) | 19.2 (87.7) | 4.8 | $3.75 \times 10^3$ |
| 13 | 0.945 (6.94) | 20.0 (138) | 17.7 (84.5) | 9.5 | $7.98 \times 10^3$ |
| 14 | 0.472 (3.47) | 20.0 (138) | 18.9 (92.3) | 18.8 | $1.27 \times 10^4$ |

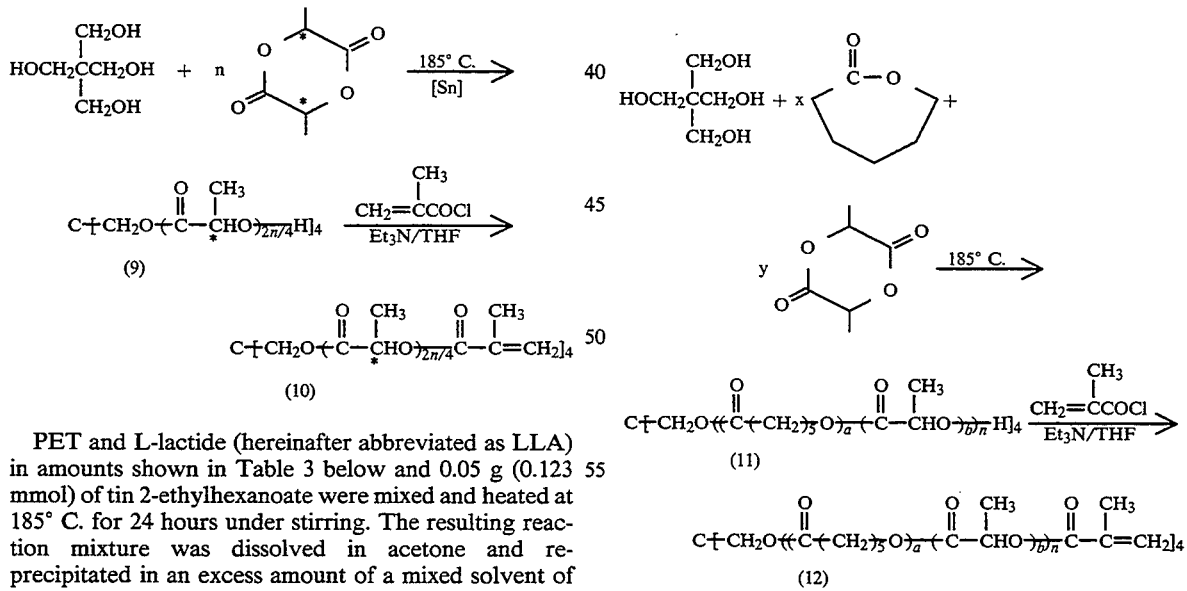

PET and L-lactide (hereinafter abbreviated as LLA) in amounts shown in Table 3 below and 0.05 g (0.123 mmol) of tin 2-ethylhexanoate were mixed and heated at 185° C. for 24 hours under stirring. The resulting reaction mixture was dissolved in acetone and reprecipitated in an excess amount of a mixed solvent of hexane/diethyl ether/methanol (1/1/0.05 by volume) to obtain a precursor comprising poly-L-lactide represented by the chemical formula (9) above as a white powder.

$^1$H-NMR, δ(CDCl$_3$, ppm); 1.52 (m, —CH (C″H″$_3$) O—), 4.05 (t, —C″H″$_2$O—), 5.14 (q, C″H″(CH$_3$)O—) . IR (cm$^{-1}$); 3550 (—OH), 2990, 2940, 1760 (C=O), 1720, 1450, 1380, 1360, 1270, 1190, 1130, 1100, 1050, 870, 760.

PET, CL and LA in amounts shown in Table 4 below were mixed and heated at 185° C. for 3 days under stirring. The resulting reaction mixture was dissolved in acetone and reprecipitated in an excess amount of a mixed solvent of hexane/diethyl ether/methanol (1/1/0.05 by volume) to obtain a precursor comprising a CL/LA random copolymer represented by the chemical formula (11) above as a white powder.

1H-NMR, δ(CDCl3, ppm); 1.52 (m, —CH2(C"H"2)3CH2O—), —CH(C"H"3)O—), 2.31 (t, —COC"H"2—), 4.12 (t, —C"H"2O—), 5.15 (q, C"H"(CH3)O—). IR (cm⁻¹); 3490 (—OH), 2960, 2890, 1740 (C═O), 1460, 1370, 1270, 1200, 1170, 1140, 1100, 1050, 970, 870, 750.

The resulting precursor was dissolved in tetrahydrofuran, and about 10 molar equivalent of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (12) above as a white powder. An amount of the product, a yield (%), an average polymerization degree determined from a peak area ratio of ¹H-NMR spectrum, and a weight-average molecular weight determined based on the polystyrene standards by GPC are shown in Table 4 below.

¹H-NMR, δ(CDCl3, ppm); 1.52 (m, —CH2 (C"H"2)3CH2—), —CH(C"H"3)O—), 1.90 (s, —C(C"H"3)═CH2), 2.31 (t, —COC"H"2—), 4.12 (t, —C"H"2O—), 5.16 (q, C"H"(CH3)O—), 5.58 (d, —C(CH3)═C"H"2), 6.11 (d, —C (CH3)═C"H"2). IR (cm⁻¹); 2960, 2890, 1740 (C═O), 1640 (C═C), 1460, 1370, 1270, 1200, 1170, 1140, 1100, 1050, 970, 870, 810, 750 .

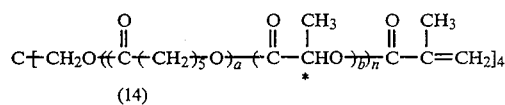

(14)

PET, CL and LLA in amounts shown in Table 5 below and 0.05 g (0.123 mmol) of tin 2-ethylhexanoate were mixed, and heated at 185 °C. for 3 days under stirring. The resulting reaction mixture was dissolved in acetone and reprecipitated in an excess amount of a mixed solvent of hexane/diethyl ether/methanol (1/1/0.5 by volume) to obtain a precursor comprising a CL/LLA random copolymer represented by the chemical formula (13) above. ¹H-NMR, δ(CDCl3, ppm); 1.54 (m, —CH2(C"H"2)3CH2O—, —CH(C"H"3)O—), 2.31 (t, —COC"H"2—), 4.13 (t, —C"H"2O—), 5.14 (q, C"H"(CH3)O—). IR (cm⁻¹); 3530 (—OH), 2960, 2900, 1750 (C═O), 1460, 1380, 1360, 1270, 1200, 1170, 1140, 1100, 1050, 970, 870, 750.

The resulting precursor was dissolved in tetrahydrofuran, and about 10 molar equivalent of methacryloyl chloride and triethylamine were added to the solution, followed by stirring for 24 hours at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a struc-

TABLE 4

| Ref. Example No. | Amount of PET g (mmol) | Amount of CL g (mmol) | Amount of LA g (mmol) | Yield, g (% yield) | Composition a/b mol % | Average Polymerization Degree | Weight-average Molecular Weight |
|---|---|---|---|---|---|---|---|
| 15 | 0.945 (6.94) | 7.83 (68.6) | 16.0 (111) | 23.4 (97.9) | 42/58 | 8.8 | 9.47 × 10³ |
| 16 | 0.945 (6.94) | 31.3 (274) | 4.00 (27.7) | 35.6 (98.3) | 91/9 | 9.5 | 1.01 × 10⁴ |

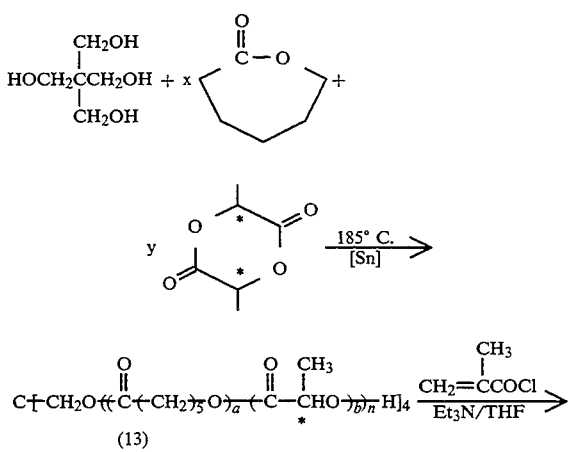

ture represented by the chemical formula (14) above as a white powder. An amount of the product, a yield (%), an average polymerization degree determined from a peak area ratio of ¹H-NMR spectrum, and a weight-average molecular weight determined based on the polystyrene standards by GPC are shown in Table 5 below.

¹H-NMR, δ(CDCl3, ppm); 1.54 (m, —CH2(C"H"2)3CH2O—, —CH(C"H"3)O—), 1.96 (s, —C(C"H"3)═CH2), 2.31 (t, —COC"H"2—), 4.13 (t, —C"H"2O—), 5.14 (q, C"H"(CH3)O—) 5.63 (d, —C(CH3)═C"H"2), 6.12 (d, —C(CH3)═C"H"2). IR (cm⁻¹); 2960, 2900, 1750 (C═O), 1640 (C═C), 1460, 1420, 1380, 1360, 1270, 1200, 1170, 1140, 1100, 1050, 960, 870, 820, 750.

TABLE 5

| Ref. Example No. | Amount of PET g (mmol) | Amount of CL g (mmol) | Amount of LLA g (mmol) | Yield, g (% yield) | Composition a/b mol % | Average Polymerization Degree | Weight-average Molecular Weight |
|---|---|---|---|---|---|---|---|
| 17 | 0.945 (6.94) | 7.83 (55.5) | 16.0 (111) | 19.4 (78.4) | 31/69 | 4.8 | 6.7 × 10³ |

TABLE 5-continued

| Ref. Example No. | Amount of PET g (mmol) | Amount of CL g (mmol) | Amount of LLA g (mmol) | Yield, g (% yield) | Composition a/b mol % | Average Polymerization Degree | Weight-average Molecular Weight |
|---|---|---|---|---|---|---|---|
| 18 | 0.945 (6.94) | 15.8 (139) | 10.0 (69.4) | 22.8 (85.1) | 42/58 | 7.3 | $7.05 \times 10^3$ |
| 19 | 0.945 (6.94) | 31.3 (222) | 4.00 (27.7) | 35.8 (98.7) | 86/14 | 9.3 | $1.36 \times 10^4$ |

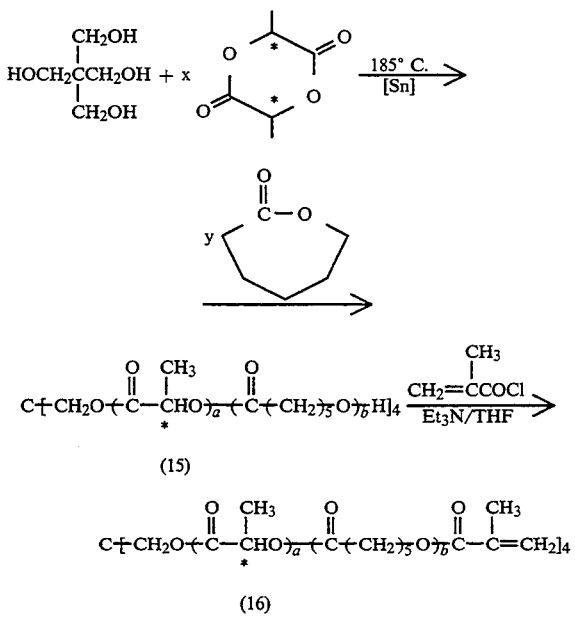

(15)

(16)

PET and LLA in amounts shown in Table 6 below and 0.05 g (0.123 mmol) of tin 2-ethylhexanoate were mixed and heated at 185° C. for 24 hours under stirring.

Then, in an amount shown in Table 6 below was added to the resulting reaction solution, and the mixture was further heated at 185 ° C. for 24 hours under stirring. The resulting reaction mixture was dissolved in acetone and reprecipitated in an excess amount of a mixed solvent of hexane/diethyl ether/methanol (1/1/0.01 by volume) to obtain a precursor comprising a LLA/CL block copolymer represented by the chemical formula (15) above as a white powder.

$^1$H-NMR, δ(CDCl$_3$, ppm); 1.54 (m, —CH$_2$(C″H″$_2$)$_3$CH$_2$O—), —CH(C″H″$_3$)O—), 2.31 (t, —COC″H″$_2$—), 4.06 (t, —C″H″$_2$O—), 5.14 (q, C″H″(CH$_3$)O—). IR (cm$^{-1}$); 3510 (—OH), 2940, 2870, 1730 (C=O), 1460, 1420, 1380, 1360, 1250, 1190, 1130, 1090, 1040, 960, 870, 740.

The resulting precursor was dissolved in tetrahydrofuran, and about 10 molar equivalent of methacryloyl chloride and triethylamine were added to the solution, followed by stirring for 24 hours at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (16) above as a white powder. An amount of the product, a yield (%), an average polymerization degree determined from a peak area ratio of $^1$H-NMR spectrum, and a weight-average molecular weight determined based on the polystyrene standards by GPC are shown in Table 6 below.

$^1$H-NMR, δ(CDCl$_3$, ppm); 1.54 (m, —CH$_2$(C″H″$_2$)$_3$CH$_2$O —, —CH(C″H″$_3$)O—), 1.96 (s, —C(C″H″$_3$)=CH$_2$), 2.31 (t, —COC″H″$_2$—), 4.06 (t, —C″H″$_2$O—), 5.14 (q, C″H″(CH$_3$)O—) , 5.63 (d, —C(CH$_3$)=C″H″$_2$) , 6.12 (d, —C(CH$_3$)=C″H″$_2$). IR (cm$^{-1}$); 2940, 2870, 1740 (C=O), 1640 (C=C), 1460, 1420, 1380, 1250, 1190, 1130, 1110, 1040, 960, 870, 810, 740.

TABLE 6

| Ref. Example No. | Amount of PET g (mmol) | Amount of LLA g (mmol) | Amount of CL g (mmol) | Yield, g (% yield) | Composition a/b mol % | Average Polymerization Degree | Weight-average Molecular Weight |
|---|---|---|---|---|---|---|---|
| 20 | 0.189 (1.39) | 2.00 (13.9) | 3.13 (27.4) | 4.11 (80.2) | 42/58 | 8.5 | $1.07 \times 10^4$ |
| 21 | 0.113 (0.833) | 1.20 (8.33) | 3.75 (32.9) | 4.56 (92.0) | 21/79 | 13.2 | $1.58 \times 10^4$ |
| 22 | 0.456 (0.486) | 4.83 (4.86) | 30.6 (38.3) | 33.0 (89.8) | 20/80 | 23.8 | $2.34 \times 10^4$ |
| 23 | 0.0946 (0.695) | 2.00 (13.9) | 3.13 (27.4) | 4.87 (96.8) | 42/58 | 23.2 | $1.94 \times 10^4$ |
| 24 | 0.0473 (0.347) | 2.00 (13.9) | 3.13 (27.4) | 4.36 (85.6) | 47/53 | 37.3 | $2.24 \times 10^4$ |
| 25 | 0.199 (1.46) | 2.10 (14.6) | 20.0 (175) | 19.9 (89.5) | 14/86 | 34.3 | $4.58 \times 10^4$ |
| 26 | 0.199 (1.46) | 4.21 (29.2) | 20.0 (175) | 20.5 (84.2) | 25/75 | 38.8 | $4.08 \times 10^4$ |

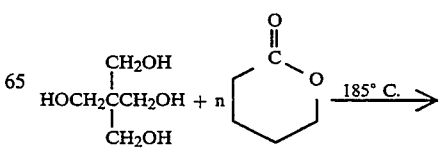

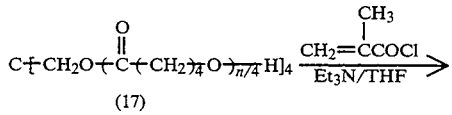

(17)

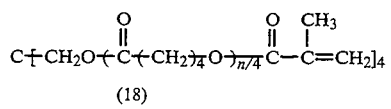

(18)

polystyrene standards by GPC are shown in Table 7 below.

$^1$H-NMR, δ(CDCl$_3$, ppm); 1.58 (m, —CH$_2$(C″H″$_2$)$_2$CH$_2$O—), 1.90 (s, —C(C″H″$_3$)=CH$_2$), 2.31 (t, —COC″H″$_2$—), 4.06 (t, —C″H″$_2$O—), 5.58 (d, —C(CH$_3$)=C″H″$_2$), 6.12 (d, —C(CH$_3$)=C″H″$_2$). IR (cm$^{-1}$); 2960, 2890, 1730 (C=O), 1640 (C=C), 1470, 1420, 1400, 1380, 1320, 1260, 1190, 1170, 1100, 1070, 1050, 950, 920, 810, 730.

TABLE 7

| Ref. Example No. | Amount of PET g (mmol) | Amount of VL g (mmol) | Yield, g (% yield) | Average Polymerization Degree | Weight-average Molecular Weight |
|---|---|---|---|---|---|
| 27 | 0.102 (0.749) | 3.00 (30.0) | 2.52 (81.1) | 9.5 | 3.00 × 10$^4$ |
| 28 | 0.051 (0.374) | 3.00 (30.0) | 2.43 (79.6) | 19.5 | 6.18 × 10$^4$ |
| 29 | 0.340 (2.50) | 30.0 (300) | 28.8 (94.9) | 28.8 | 9.00 × 10$^4$ |

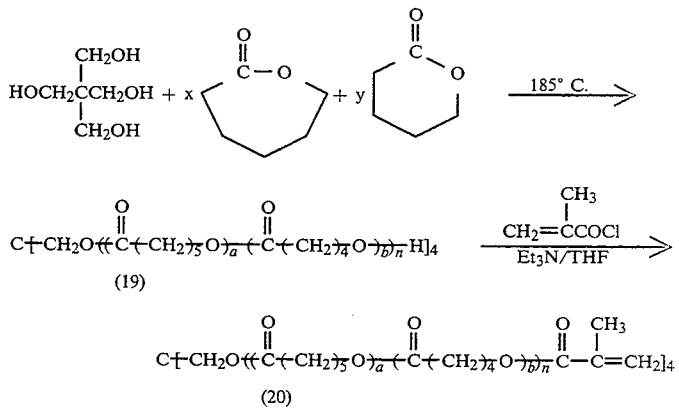

PET and δ-valerolactone (hereinafter abbreviated as VL) in amounts shown in Table 7 below were mixed and heated at 185° C. for 3 days under stirring. The resulting reaction mixture was dissolved in acetone and reprecipitated in an excess amount of a mixed solvent of hexane/diethyl ether (1/1 by volume) to obtain a precursor comprising a poly-δ-valerolactone represented by the chemical formula (17) above as a white powder.

$^1$H-NMR, δ(CDCl$_3$, ppm); 1.58 (m, —CH$_2$(C″H″$_2$)$_2$CH$_2$O—), 2.31 (t, COC″H″$_2$—), 4.05 (t, —C″H″$_2$O—). IR (cm$^{-1}$); 3520 (—OH), 2960, 2890, 1730 (C=O), 1470, 1420, 1400, 1380, 1320, 1260, 1190, 1170, 1100, 1070, 1050, 950, 920, 730.

The resulting precursor was dissolved in tetrahydrofuran, and about 10 molar equivalent of methacryloyl chloride and triethylamine were added to the solution, followed by stirring for 3 days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (18) above as a white powder. An amount of the product, a yield (%), an average polymerization degree determined from a peak area ratio of $^1$H-NMR spectrum, and a weight-average molecular weight determined based on the PET, CL and VL in amounts shown in Table 8 below were mixed and heated at 185° C. for 3 days under stirring. The resulting reaction mixture was dissolved in acetone and reprecipitated in an excess amount of a mixed solvent of hexane/diethyl ether (1/1 by volume) to obtain a precursor comprising a CL/VL random copolymer represented by the chemical formula (19) above as a white powder. $^1$H-NMR, δ(CDCl$_3$, ppm); 1.58 (m, —CH$_2$ (C″H″$_2$)$_3$CH$_2$O—, CH$_2$(C″H″$_2$)$_2$CH$_2$O —), 2.30 (t, —COC″H″$_2$—), 4.11 (t, —C″H″$_2$O—). IR (cm$^{-1}$); 3520 (—OH), 2940, 2870, 1730 (C=O), 1470, 1440, 1420, 1390, 1300, 1240, 1190, 1170, 1100, 1060, 1040, 960, 930, 730.

The resulting precursor was dissolved in tetrahydrofuran, and about 10 molar equivalent of methacryloyl chloride and triethylamine were added to the solution, followed by stirring for days at room temperature. Then, after distilling off the solvent and unreacted methacryloyl chloride and triethylamine, ethyl acetate was added thereto, and the salt thus produced was separated by filtration. The filtrate was concentrated and reprecipitated in an excess amount of a mixed solvent of hexane/diethyl ether/methanol (18/1/1 by volume) to obtain a tetrafunctional macromonomer having a structure represented by the chemical formula (20) above as a white powder. An amount of the product, a yield (%), an average polymerization degree determined from a peak area ratio of $^1$H-NMR spectrum, and a weight-average molecular weight determined based on the polystyrene standards by GPC are shown in Table 8 below.

$^1$H-NMR, δ(CDCl$_3$, ppm); 1.58 (m, —CH$_2$(C″H″$_2$)$_3$CH$_2$O—, CH$_2$(C″H″$_2$)$_2$CH$_2$—), 1.90 (s, —C(C″H″$_3$)=CH$_2$), 2.31 (t, —COC″H″$_2$—), 4.12 (t, —C″H″$_2$O—), 5.16 (q, C″H″(CH$_3$)O—), 5.58 (d, —C(CH$_3$)=C″H″$_2$), 6.11 (d, —C(CH$_3$)=C″H″$_2$). IR (cm$^{-1}$); 2940, 2870, 1730 (C=O), 1640 (C=C), 1470, 1440, 1420, 1390, 1300, 1240, 1190, 1170, 1100, 1060, 1040, 960, 930, 840, 730.

TABLE 8

| Ref. Example No. | Amount of PET g (mmol) | Amount of CL g (mmol) | Amount of VL g (mmol) | Yield, g (% yield) | Composition a/b mol % | Average Polymerization Degree | Weight-average Molecular Weight |
|---|---|---|---|---|---|---|---|
| 30 | 0.086 (0.599) | 5.47 (47.9) | 1.20 (12.0) | 5.29 (78.3) | 80/20 | 22.4 | 4.68 × 10$^4$ |
| 31 | 1.19 (8.74) | 80.0 (701) | 3.51 (35.0) | 75.9 (89.6) | 95/5 | 19.9 | 3.38 × 10$^4$ |

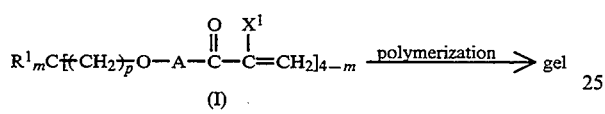

$$R^1{}_mC\text{\textlbrackdbl}(CH_2)_p\overline{O-A-\overset{O}{\overset{\|}{C}}-\overset{X^1}{\overset{|}{C}}=CH_2]_{4-m}} \xrightarrow{\text{polymerization}} \text{gel}$$

(I)

1 g of the trifunctional or tetrafunctional polyester macromonomer obtained in each of Referential Examples 1 to 31, 0.01 g of N,N-dimethyl-p-toluidine and 0.01 of camphorquinone were dissolved in 1 g of xylene. A spacer made from polytetrafluoroethylene having a thickness of 0.1 mm was inserted between two glass plates each having a size of 10 cm × 10 cm, and the above-prepared xylene solution was injected into the space between the glass plates. The glass plates were uniformly irradiated with visible light at an intensity of about 0.5 mW/cm$^2$ for 10 minutes thereby polymerizing the macromonomer to obtain a colorless transparent gel membrane having a thickness of from 60 to 90 μm. The membrane was immersed in acetone for about 8 hours to remove the initiator and sensitizer contained wherein and then thoroughly dried under reduced pressure.

Test Example 1 (Measurement of Mechanical Properties)

A part of the polyester gel membrane obtained in each of Referential Examples 32 to 62 was subjected to a tensile test, and the tensile modulus, the tensile strength and the maximum elongation percentage were calculated from the stress-strain diagram obtained by the tensile test. The results obtained are shown in Table 9.

As is noted from the results shown in Table 9, gel membranes having various modulus, strength and elongation percentage can be prepared from the polyfunctional macromonomers having different constituting components of the polymer chain and average polymerization degrees.

TABLE 9

| Ref. Example No. | Ref. Example No. of starting Macromonomer | Tensile Modulus MPa | Tensile Strength MPa | Maximum Elongation Percentage % |
|---|---|---|---|---|
| 32 | 1 | 3.72 | 0.904 | 62.3 |
| 33 | 2 | 109 | 8.89 | 195 |
| 34 | 3 | 322 | 9.38 | 239 |
| 35 | 4 | 145 | 7.77 | 89.0 |
| 36 | 5 | 16.3 | 2.70 | 25.8 |
| 37 | 6 | 16.0 | 1.76 | 45.4 |
| 38 | 7 | 104 | 9.39 | 196 |
| 39 | 8 | 144 | 9.04 | 45.4 |
| 41 | 10 | 1050 | 21.9 | 71.9 |
| 42 | 11 | 55.9 | 6.43 | 380 |
| 43 | 12 | 1310 | 32.2 | 13.6 |
| 44 | 13 | 1610 | 31.6 | 7.37 |
| 45 | 14 | 831 | 38.1 | 10.3 |
| 46 | 15 | 11.2 | 6.57 | 182 |
| 47 | 16 | 4.64 | 1.21 | 56.4 |
| 48 | 17 | 16.9 | 8.96 | 196 |
| 49 | 18 | 0.732 | 0.473 | 109 |
| 50 | 19 | 2.27 | 0.683 | 102 |
| 51 | 20 | 4.53 | 1.89 | 52.7 |
| 52 | 21 | 45.6 | 4.19 | 158 |
| 53 | 22 | 109 | 14.7 | 883 |
| 54 | 23 | 2.27 | 1.04 | 90.2 |
| 55 | 24 | 3.02 | 0.90 | 57.5 |

Test Example 2 (Thermal Properties)

A part of the polyester gel membrane obtained in Each of Referential Examples 32 to 62 was tested for a transition temperature of gel using a differential scanning calorimeter, and the results obtained are shown in Table 10 below. The transition temperatures in the Table represent maximum points of heat absorption peaks.

As is noted from the results shown in Table 10, each of the gels showed a phase transition temperature of high transition enthalpy, and the transition temperature was found to be different depending upon the difference in the constituting components of the polyester chain and the average polymerization degree.

TABLE 10

| Ref. Transition Example No. | Ref. Example No. of starting Macromonomer | Transition Temperature °C. | Enthalpy mJ/mg |
|---|---|---|---|
| 37 | 6 | 41.2 | 15.0 |
| 38 | 7 | 44.0 | 30.0 |
| 39 | 8 | 50.3 | 52.7 |
| 40 | 9 | 55.0 | 59.2 |
| 53 | 22 | 45.5 | 31.3 |
| 56 | 25 | 49.0 | 49.4 |
| 57 | 26 | 46.3 | 32.5 |
| 58 | 27 | 38.7 | 27.1 |
| 59 | 28 | 46.2 | 49.0 |
| 60 | 29 | 51.4 | 58.7 |
| 61 | 30 | 35.8 | 34.3 |
| 62 | 31 | 46.6 | 44.1 |

EXAMPLES 1 TO 3

The gel membrane obtained in each of Referential Examples 38, 39 and 53 was put between two chambers of a two-chamber diffusion cell (effective cross-sectional area: 0.95 cm², and 2 ml of a phosphate buffer adjusted to pH 7.4 containing a saturated amount (about 7 mg, about 0.3 wt %) of an anti-inflammatory agent, indomethacin, was placed into the donor section, and 2 ml of a phosphate buffer adjusted to pH 7.4 was placed into the receptor section. The whole of the cell was then dipped into a thermostat tank adjusted to a predetermined temperature. The temperature of the tank was maintained at a constant temperature in the range of from 20 ° C. to 55° C. in a step of 5 ° C. The receptor solution was sampled from the receptor section in every 20 minutes, and indomethacin permeated through the gel membrane was quantitatively determined by high performance liquid chromatography. The change in the concentration of permeated indomethacin with the lapse of time was determined from the slope of permeation curve in a stationary state obtained by plotting the accumulated amount of indomethacin permeated into the receptor section at the sampling time with respect of time passed. Then, from the change in the concentration of indomethacin with the time at each of the test temperatures, a permeation coefficient P of indomethacin permeated through the membrane was calculated by the following equation (1):

$$P = (V\, dC/dt)/(A\, Cv) \quad (1)$$

wherein:

V: Volume of the receptor section dC/dt: Change in concentration of indomethacin in the receptor section with the time passed A: Area of membrane Cv: Concentration of indomethacin in receptor section The permeation coefficient P of indomethacin permeated through each of the gel membranes at each of the test temperatures is shown in Table 11 below. As shown in Table 11, it was found that the value of P markedly increased at a specific temperature in each of the gel membranes.

TABLE 11

| Temperature at Measurement (°C.) | Permeation Coefficient P (cm/sec) | | |
|---|---|---|---|
| | Gel Membrane of Ref. Example 38 | Gel Membrane of Ref. Example 39 | Gel Membrane of Ref. Example 53 |
| 20 | $1.01 \times 10^{-6}$ | $1.32 \times 10^{-7}$ | $1.30 \times 10^{-7}$ |
| 25 | $1.85 \times 10^{-6}$ | $1.87 \times 10^{-7}$ | $1.82 \times 10^{-7}$ |
| 30 | $3.85 \times 10^{-6}$ | $4.89 \times 10^{-7}$ | $2.12 \times 10^{-7}$ |
| 35 | $5.66 \times 10^{-6}$ | $8.53 \times 10^{-7}$ | $1.71 \times 10^{-6}$ |
| 40 | $1.52 \times 10^{-5}$ | $3.32 \times 10^{-6}$ | $5.82 \times 10^{-6}$ |
| 45 | $3.08 \times 10^{-5}$ | $2.94 \times 10^{-5}$ | $2.20 \times 10^{-5}$ |
| 50 | $4.00 \times 10^{-5}$ | $4.08 \times 10^{-5}$ | $3.31 \times 10^{-5}$ |
| 55 | $6.04 \times 10^{-5}$ | $5.57 \times 10^{-5}$ | $6.50 \times 10^{-5}$ |

EXAMPLES 4 TO 6

Figure 2:
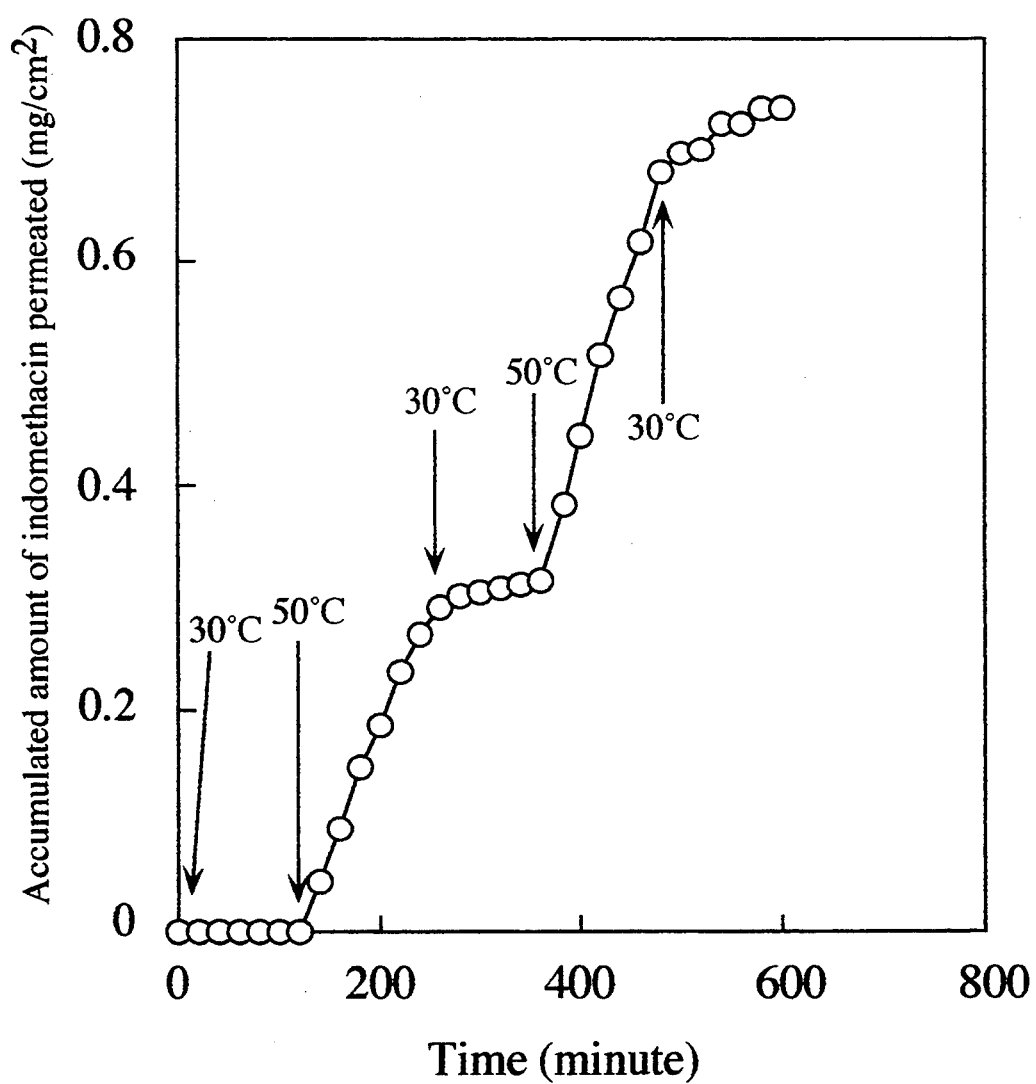
FIG. 2 is a graph showing a test result of Example 5 on permeation of indomethacin using a gel membrane produced in Referential Example 39.
Figure 3:
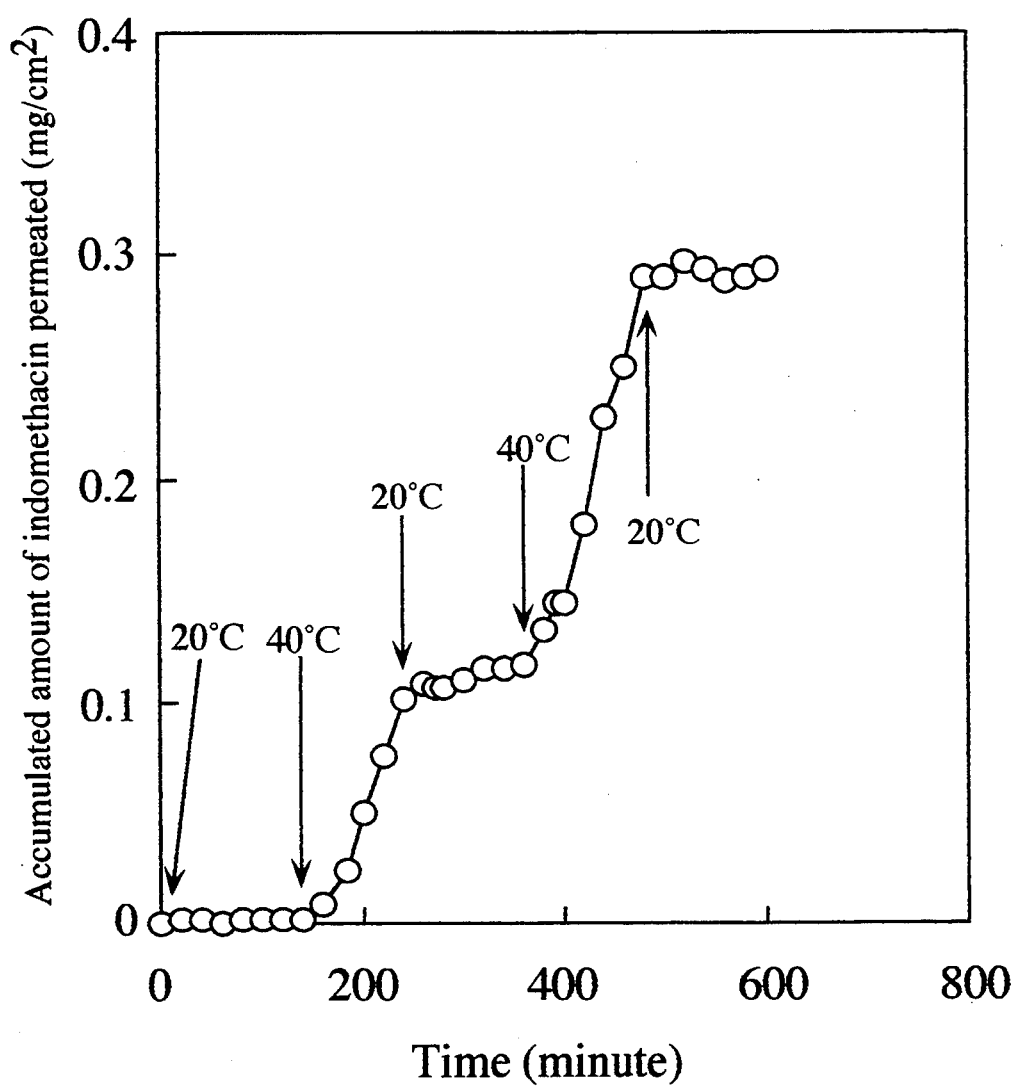
FIG. 3 is a graph showing a test result of Example 6 on permeation of indomethacin using a gel membrane produced in Referential Example 53.

The gel membrane obtained in each of Referential Examples 38, 39 and 53 was put between two chambers of a two-chamber diffusion cell (effective cross-sectional area: 0.95 cm²), and 2 ml of a phosphate buffer adjusted to pH 7.4 containing a saturated amount (about 7 mg, about 0.3 wt %) of an anti-inflammatory agent indomethacin was placed into the donor section, and 2 ml of a phosphate buffer adjusted to pH 7.4 was placed into the receptor section. The whole of the cell was then dipped into a thermostat tank adjusted to a predetermined temperature. The temperature of the tank was changed in two and half cycles at two different temperatures of 20° C.-40° C.-20° C.-40° C.-20° C. or 30° C.-50° C.-30° C.-50° C.-30° C. at an interval of 2 hours. A portion of the solution was taken out from the receptor section in every 20 minutes, and indomethacin permeated through the gel membrane was quantitatively determined by high performance liquid chromatography. The accumulated amount of indomethacin permeated into the receptor section at the sampling time was plotted with respect to time passed to obtain FIGS. 1 to 3 which correspond to the results obtained in Referential Examples 4 to 6, respectively.

As is noted from the graphs, in each of the gel membranes, the permeation rate of indomethacin markedly differ at temperatures below or above the transition temperature thereof, i.e., a lower rate in a lower temperature side and a higher rate in a higher temperature side, and it was confirmed that the indomethacin releasing rate can be controlled depending upon the change in temperature. Accordingly, these gels were found to have a function as a material for controlling the drug release responsive to changes in temperature.

EXAMPLES 7 TO 13

(4), (16) or (18) +

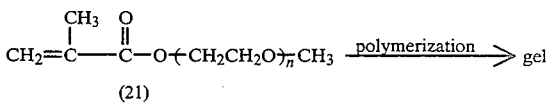

(21)

The trifunctional or tetrafunctional polyester macromonomer obtained in each of Referential Examples 8, 22, or 29, and the polyethylene glycol derivative represented by the above formula (21) were mixed in amounts described in Table 12. Then the mixture was dissolved in 1 g of xylene, together with 0.01 g of N,N-dimethyl-p-toluidine and 0.01 of camphorquinone. A spacer made from polytetrafluoroethylene having a thickness of 0.1 mm was inserted between two glass plates each having a size of 10 cm × 10 cm, and the above-prepared xylene solution was injected into the space between the glass plates. The glass plates were uniformly irradiated with visible light at an intensity of about 0.5 mW/cm² for 10 minutes thereby polymerizing the macromonomer and the polyethylene glycol derivative to obtain a colorless transparent gel membrane having a thickness of about 150 μm. The membrane was immersed in acetone for about 8 hours to remove the initiator and sensitizer contained wherein and then thoroughly dried under reduced pressure.

The polyester gel membrane obtained in each of Examples 7 to 13 was tested for a transition temperature of gel using a differential scanning calorimeter, and the results obtained are shown in Table 12 below. The transition temperatures in the Table represent maximum points of heat absorption peaks.

As is noted from the results shown in Table 12, each of the gels showed a phase transition temperature of high transition enthalpy, and the transition temperature was found to be different depending upon the difference in the constituting components of the polyester chain and the average polymerization degree.

TABLE 12

| Example No. | Starting Macromonomer Ref. Example No. | Weight (g) | PEG deriv. Average Degree of (n) | Weight (g) | Transition Temperature (°C.) | Transition Enthalpy (mJ/mg) |
|---|---|---|---|---|---|---|
| 7  | 8,  | 0.80 | 23 | 0.20 | 48.0 | 39.6 |
| 8  | 8,  | 0.90 | 23 | 0.10 | 48.6 | 51.7 |
| 9  | 8,  | 0.95 | 23 | 0.05 | 49.0 | 55.6 |
| 10 | 8,  | 0.95 | 9  | 0.05 | 50.3 | 54.7 |
| 11 | 22, | 0.90 | 23 | 0.10 | 49.8 | 44.0 |
| 12 | 22, | 0.95 | 23 | 0.05 | 50.0 | 46.0 |
| 13 | 29, | 0.95 | 23 | 0.05 | 51.6 | 63.9 |

EXAMPLES 14 TO 15

(4) +

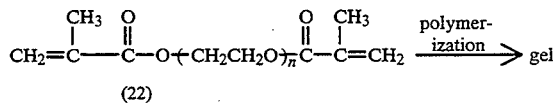

(22)

$\xrightarrow{\text{polymerization}}$ gel 1 g of the trifunctional or tetrafunctional polyester macromonomer obtained in Referential Example 8 and the polyethylene glycol derivative represented by the formula (22) were mixed in amounts described in Table 12. Then the mixture was dissolved in 1 g of xylene, together with 0.01 g of N,N-dimethyl-p-toluidine and 0.01 of camphorquinone. A spacer made from polytetrafluoroethylene having a thickness of 0.1 mm was inserted between two glass plates each having a size of 10 cm × 10 cm, and the above-prepared xylene solution was injected into the space between the glass plates. The glass plates were uniformly irradiated with visible light at an intensity of about 0.5 mW/cm² for 10 minutes thereby polymerizing the macromonomer and the polyethylene glycol derivative to obtain a colorless transparent gel membrane having a thickness of about 150 μm. The membrane was immersed in acetone for about 8 hours to remove the initiator and sensitizer contained wherein and then thoroughly dried under reduced pressure.

The resulting gel membranes were tested for a transition temperature of gel using a differential scanning calorimeter, and the results obtained are shown in Table 13 below. The transition temperatures in the Table represent maximum points of heat absorption peaks.

TABLE 13

| Ref. Example No. | Starting Macromonomer Ref. Example No. | Weight (g) | PEG deriv. Average Degree of Polym. (n) | Weight (g) | Transition Temperature (°C.) | Transition Enthalpy (mJ/mg) |
|---|---|---|---|---|---|---|
| 14 | 8, | 0.95 | 14 | 0.05 | 49.8 | 41.3 |
| 15 | 8, | 0.95 | 23 | 0.05 | 50.5 | 55.6 |

EXAMPLE 16

Figure 4:
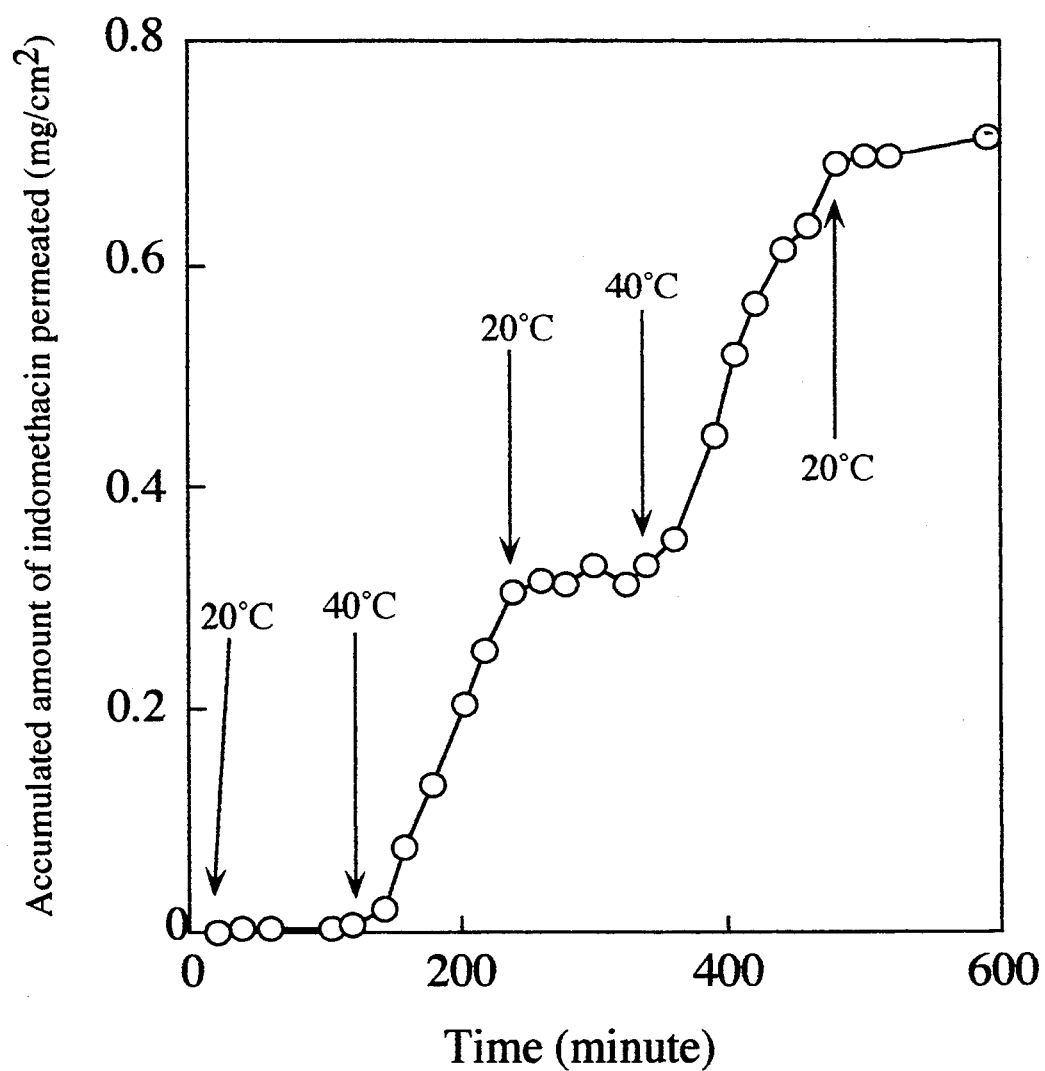
FIG. 4 is a graph showing a test result of Example 16 on permeation of indomethacin using a gel membrane produced in Example 7.
Figure 5:
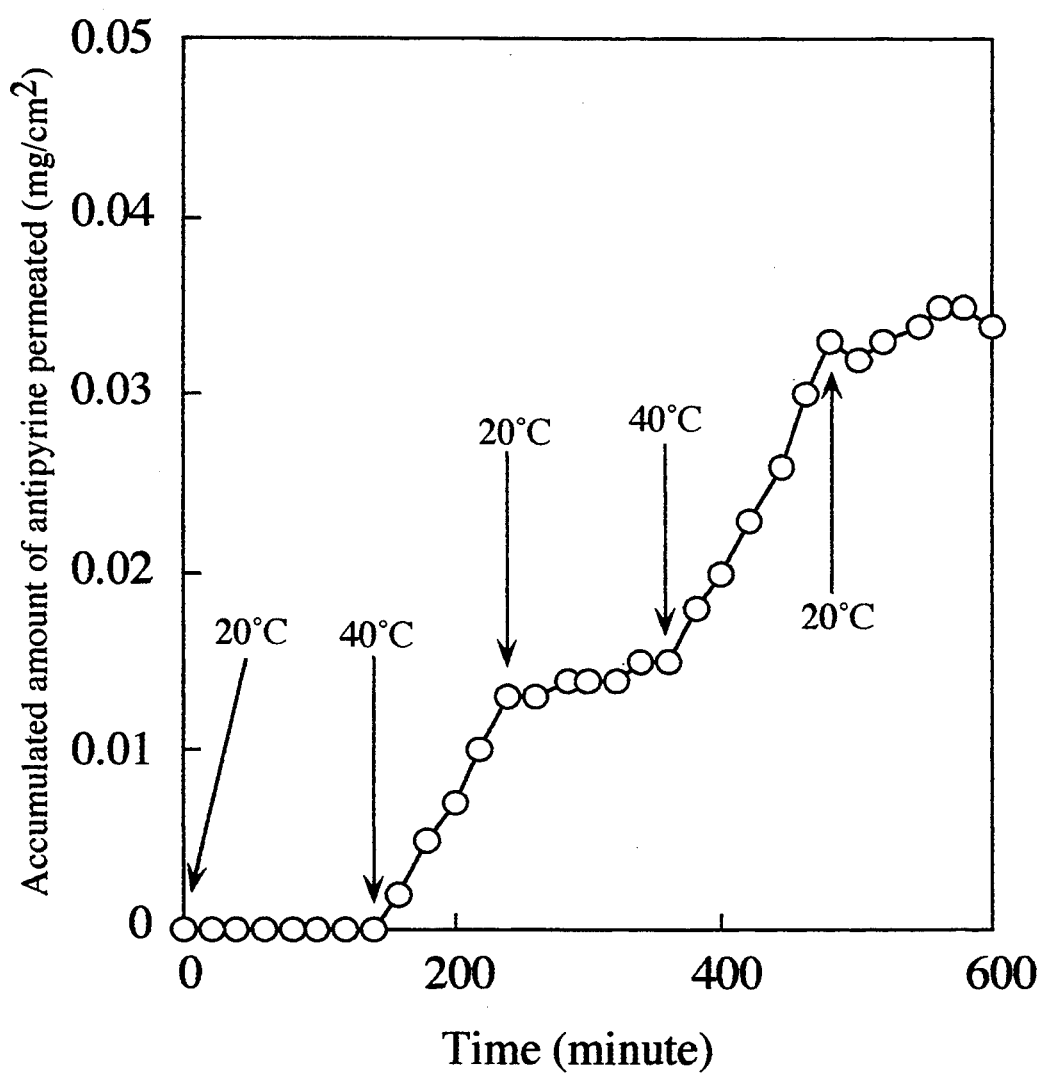
FIG. 5 is a graph showing a test result of Example 17 on permeation of antipyrine using a gel membrane produced in Referential Example 39.
Figure 6:
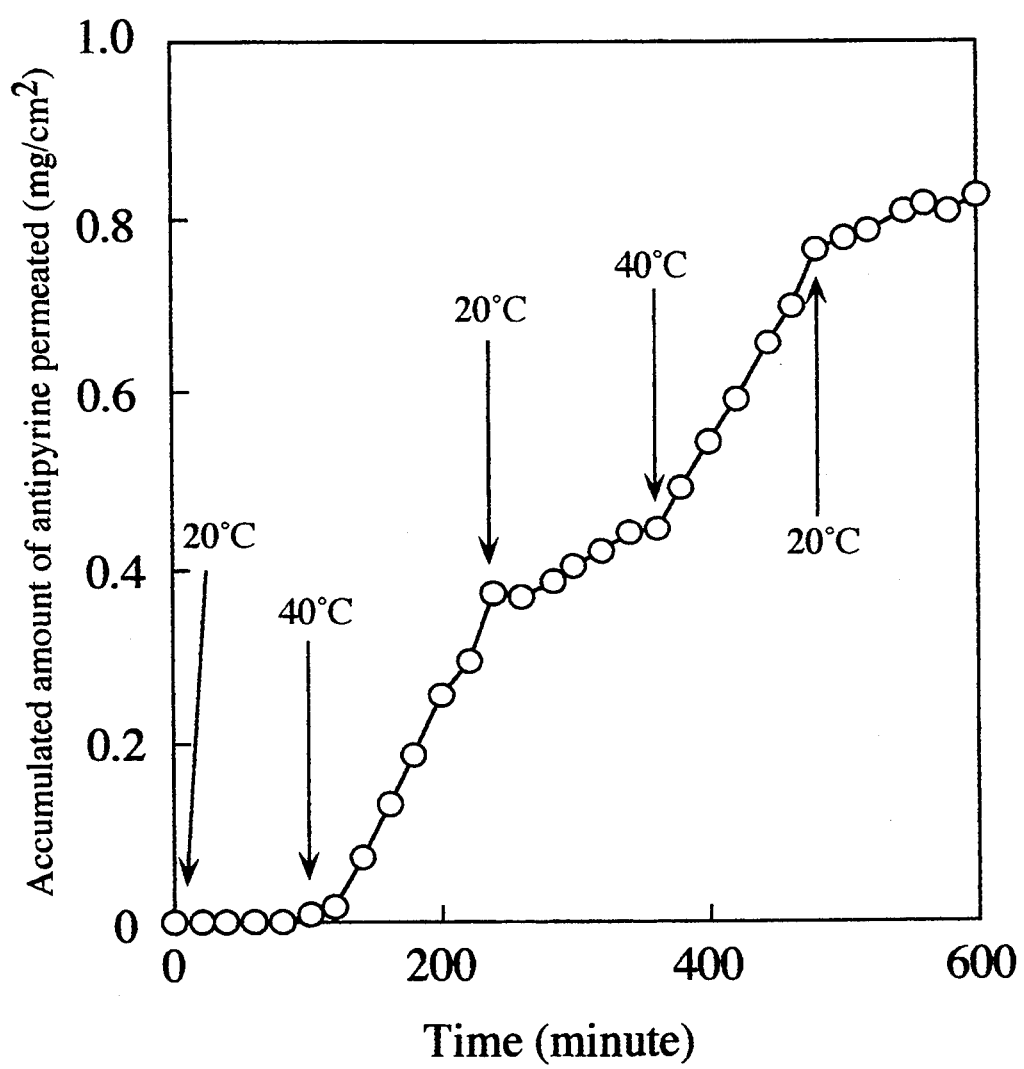
FIG. 6 is a graph showing a test result of Example 18 on permeation of antipyrine using a gel membrane produced in Example 8.
Figure 7:
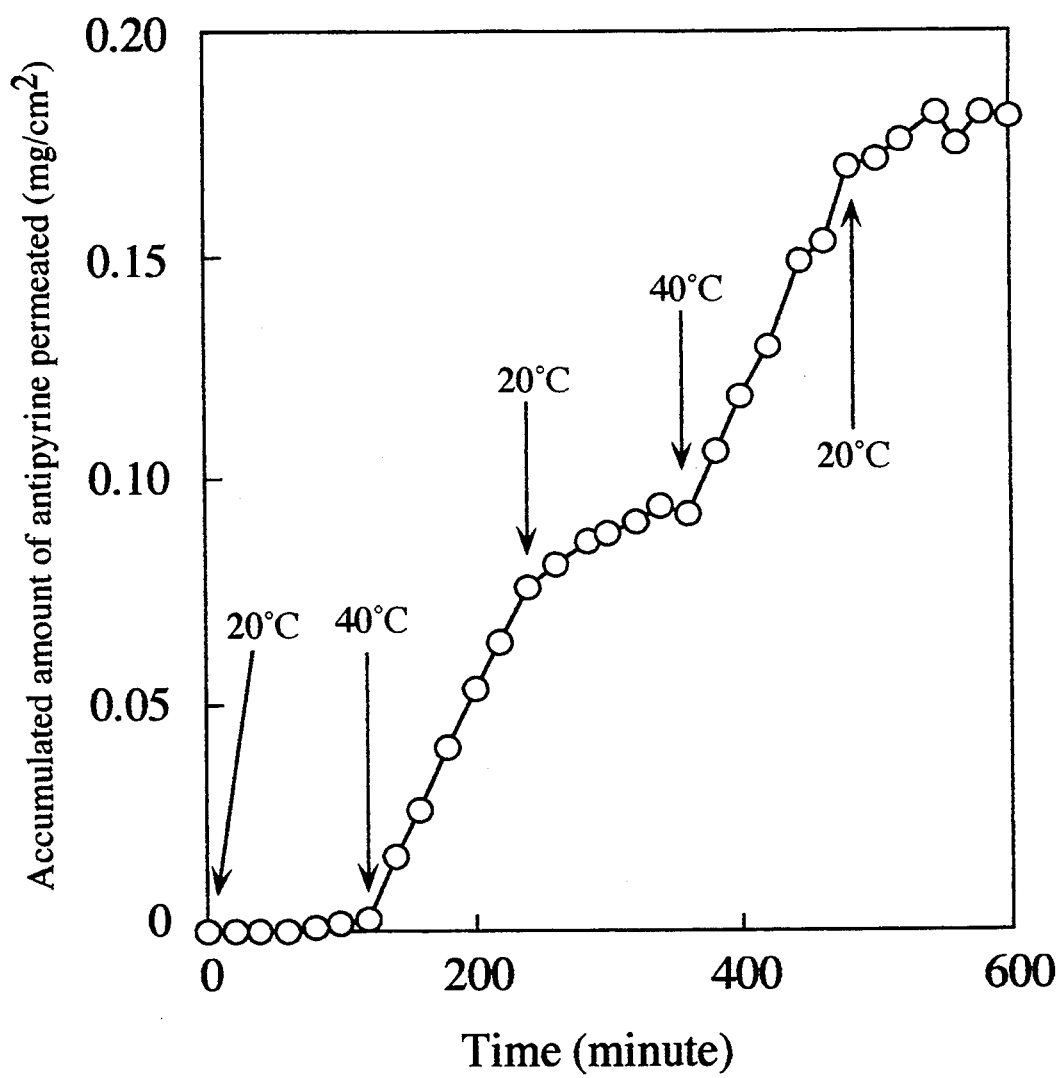
FIG. 7 is a graph showing a test result of Example 19 on permeation of antipyrine using a gel membrane produced in Example 9.
Figure 8:
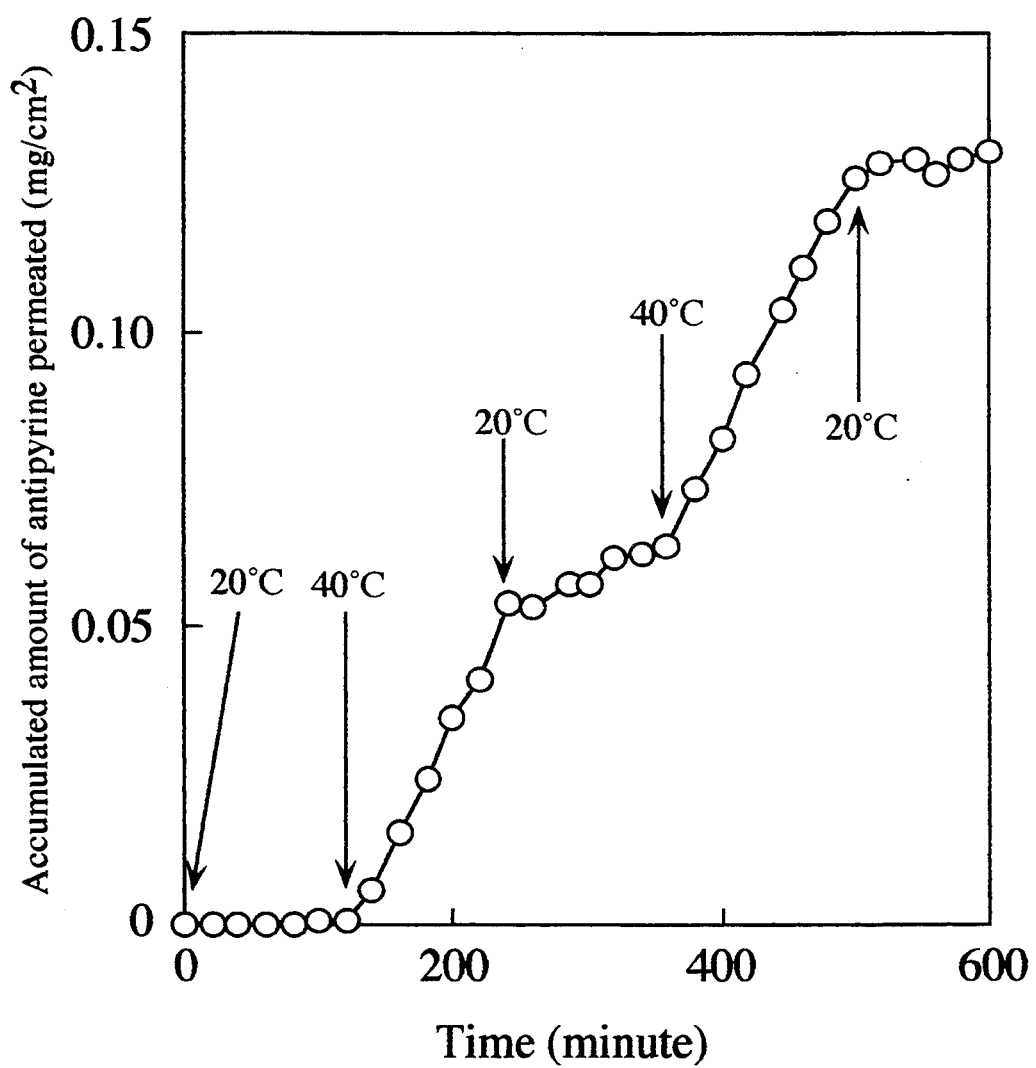
FIG. 8 is a graph showing a test result of Example 20 on permeation of antipyrine using a gel membrane produced in Example 10.
Figure 9:
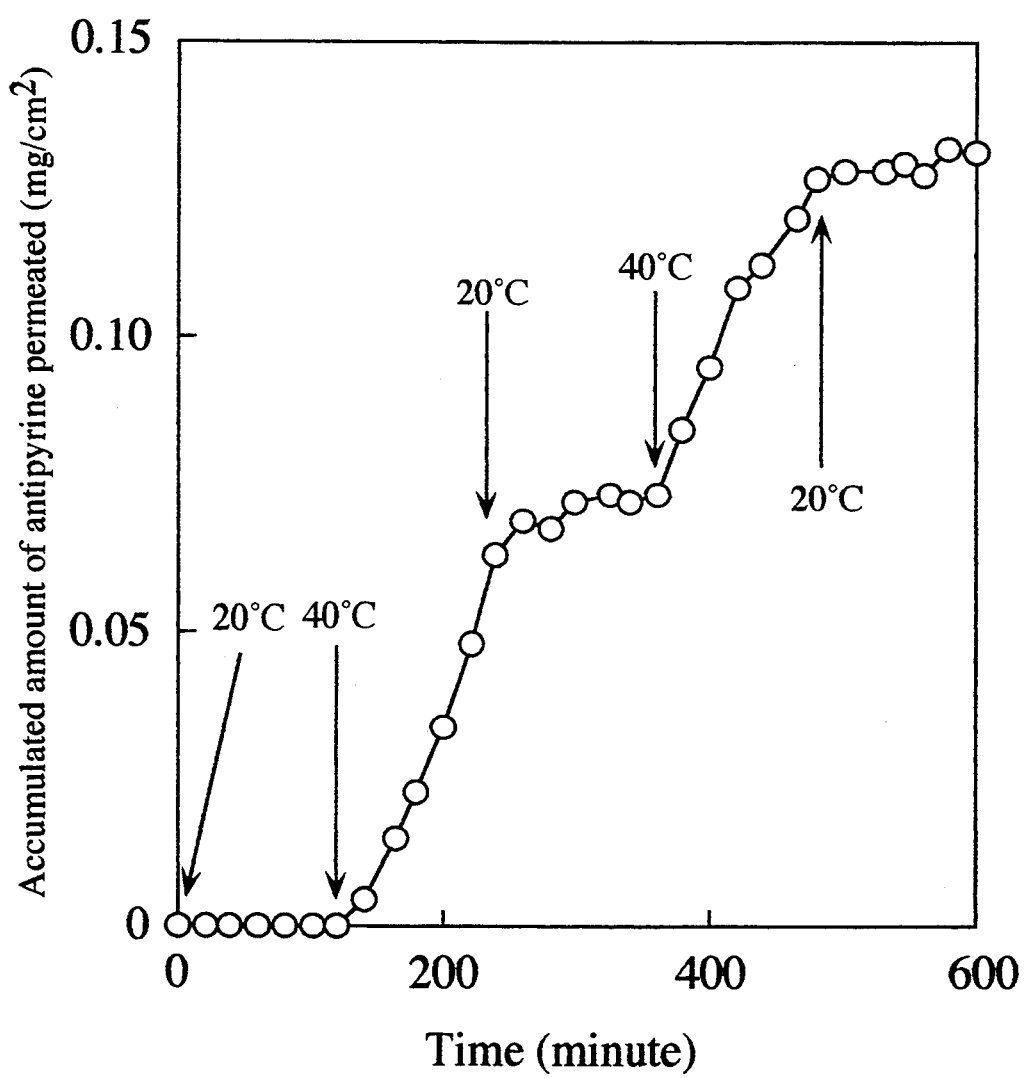
FIG. 9 is a graph showing a test result of Example 21 on permeation of antipyrine using a gel membrane produced in Example 11.
Figure 10:
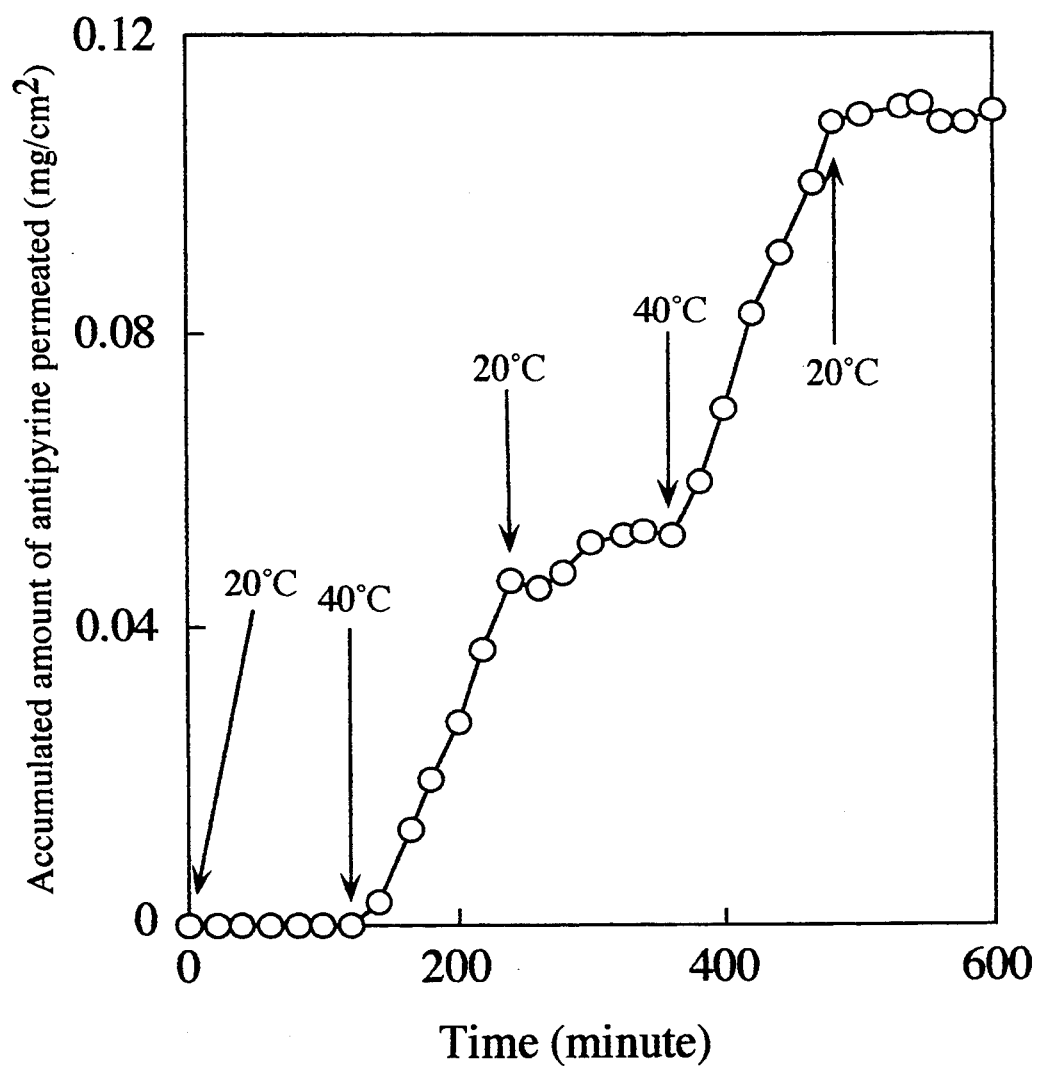
FIG. 10 is a graph showing a test result of Example 22 on permeation of antipyrine using a gel membrane produced in Example 12.
Figure 11:
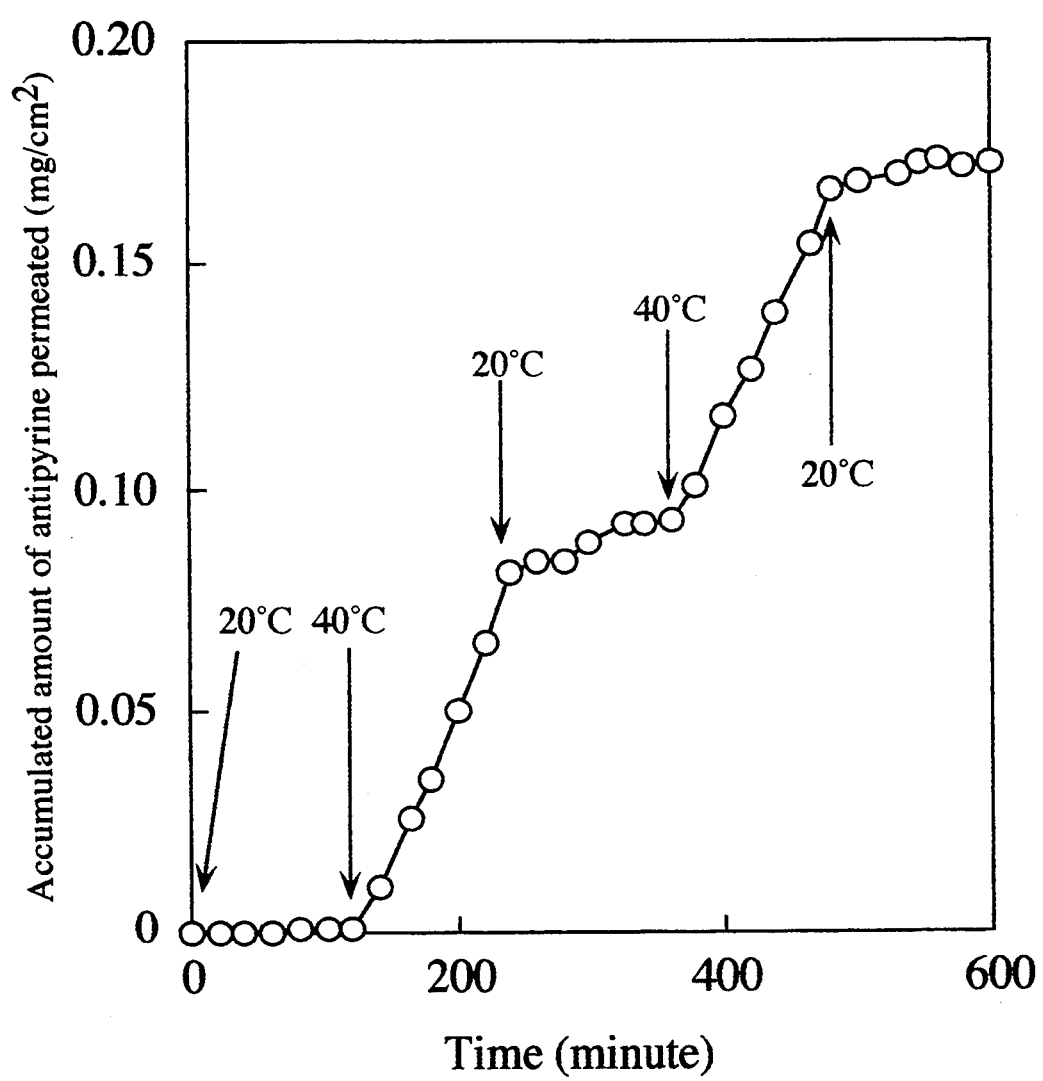
FIG. 11 is a graph showing a test result of Example 23 on permeation of antipyrine using a gel membrane produced in Example 13.
Figure 12:
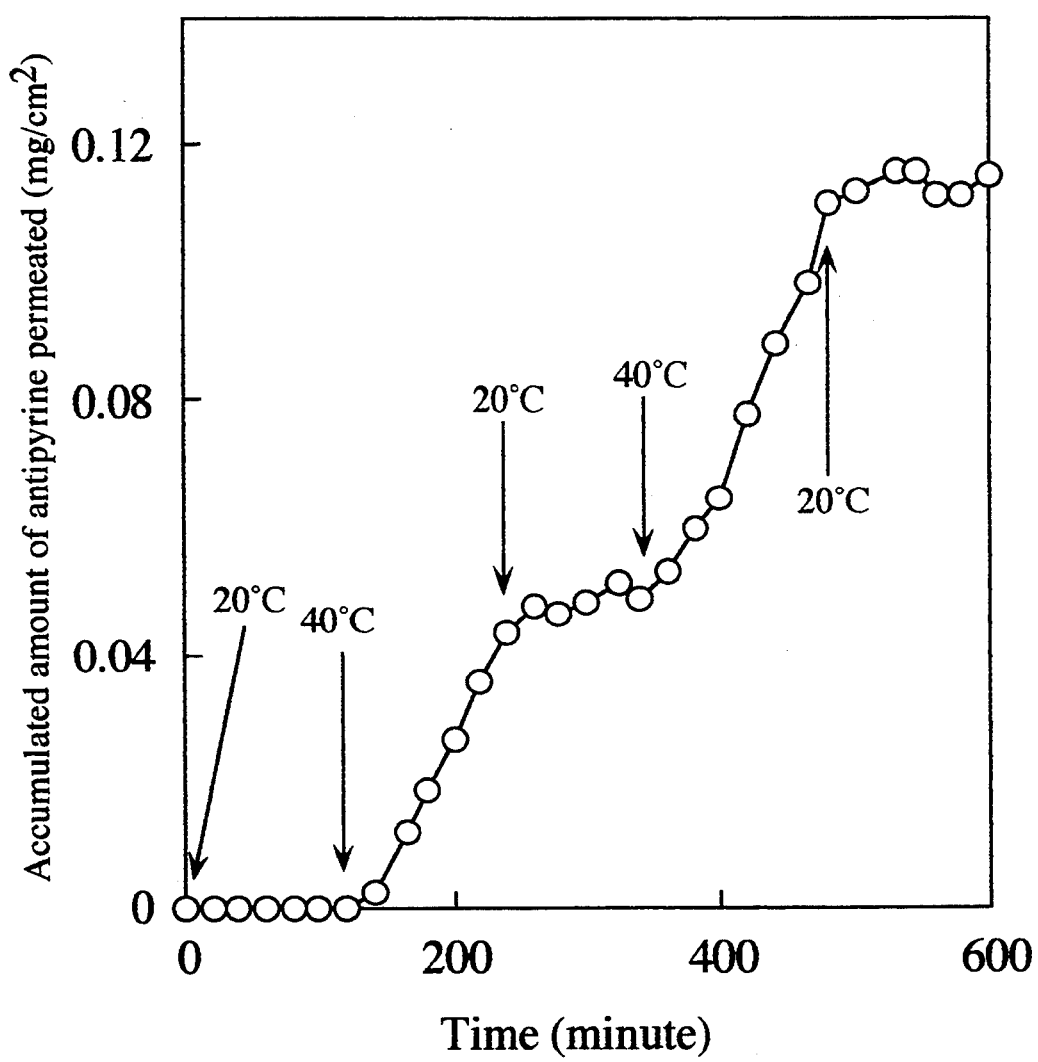
FIG. 12 is a graph showing a test result of Example 24 on permeation of antipyrine using a gel membrane produced in Example 14.
Figure 13:
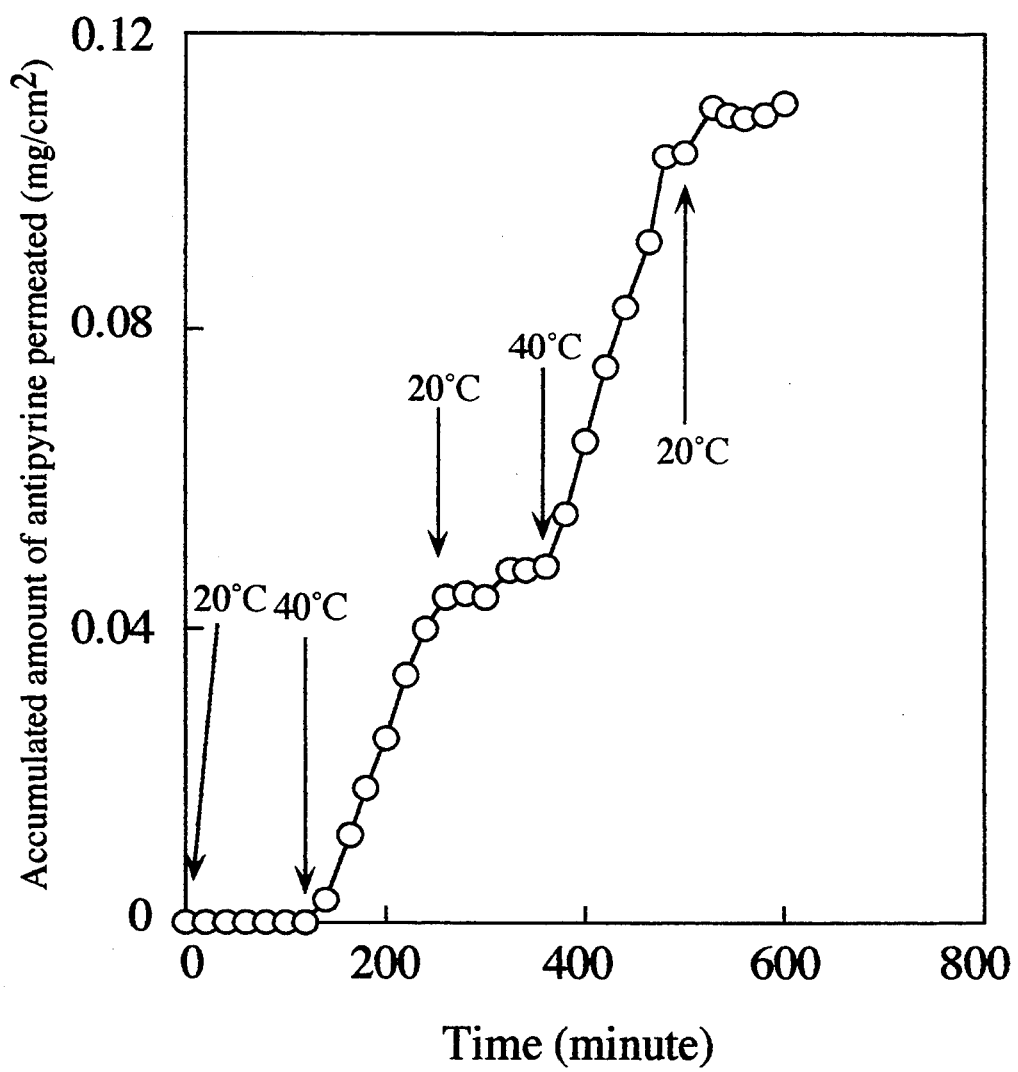
FIG. 13 is a graph showing a test result of Example 25 on permeation of antipyrine using a gel membrane produced in Example 15.

The gel membrane obtained in Example 7 was put between two chambers of a two-chamber diffusion cell (effective cross-sectional area: 0.95 cm²), and 2 ml of a phosphate buffer adjusted to pH 7.4 containing a saturated amount (about 7 mg, about 0.3 wt %) of an anti-inflammatory agent indomethacin was placed into the donor section, and 2 ml of a phosphate buffer adjusted to pH 7.4 was placed into the receptor section. The whole of the cell was then dipped into a thermostat tank adjusted to a predetermined temperature. The temperature of the tank was changed in two and half cycles at two different temperatures of 20° C.–40° C.–20° C. –40° C.–20° C. at an interval of 2 hours. A portion of the solution was taken out from the receptor section in every 20 minutes, and indomethacin permeated through the gel membrane was quantitatively determined by high performance liquid chromatography. The accumulated amount of indomethacin permeated into the receptor section at the sampling time was plotted with respect to time passed to obtain FIG. 4.

As is noted from the graph, the gel membrane shows enhanced permeation rate of indomethacin, and the permeation rate markedly differ at temperatures below or above the transition temperature thereof, i.e., a lower rate in a lower temperature side and a higher rate in a higher temperature side. Thus, it was confirmed that the indomethacin releasing rate can be controlled depending upon the change in temperature. Accordingly, these gels were found to have a function as a material for controlling the drug release responsive to changes in temperature.

EXAMPLE 17 to 25

The gel membrane obtained in each of Referential Example 39 and Examples 8 to 15 was put between two chambers of a two-chamber diffusion cell (effective cross-sectional area: 0.95 cm²), and 2 ml of a phosphate buffer adjusted to pH 7.4 containing 10 mg (0.5 wt %) of antipyrine was placed into the donor section, and 2 ml of a phosphate buffer adjusted to pH 7.4 was placed into the receptor section. The whole of the cell was then dipped into a thermostat tank adjusted to a predetermined temperature. The temperature of the tank was changed in two and half cycles at two different temperatures of 20° C.–40° C.–20° C.–40° C.–20° C. at an interval of 2 hours. A portion of the solution was taken out from the receptor section in every 20 minutes, and antipyrine permeated through the gel membrane was quantitatively determined by high performance liquid chromatography. The accumulated amount of antipyrine permeated into the receptor section at the sampling time was plotted with respect to time passed to obtain FIGS. 5 to 13 which correspond to the results obtained in Referential Examples 17 to 25, respectively.

As is noted from the graph, the gel membrane shows enhanced permeation rate of antipyrine, and the permeation rate markedly differ at temperatures below or above the transition temperature thereof, i.e., a lower rate in a lower temperature side and a higher rate in a higher temperature side. Thus, it was confirmed that the antipyrine releasing rate can be controlled depending upon the change in temperature. Accordingly, these gels were found to have a function as a material for controlling the drug release responsive to changes in temperature.

While the invention has been described in detail and with reference to specific embodiments thereof, it will be apparent to one skilled in the art that various changes and modifications can be made therein without departing from the spirit and scope thereof.

What is claimed is:

1. A pharmaceutical composition that controllably releases a drug in response to a temperature change comprising a pharmaceutically effective amount of a drug, and a polyester gel obtained by polymerizing a polyfunctional macromonomer represented by formula (I):

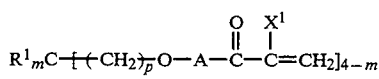

wherein $R^1$ represents a hydrogen atom or an alkyl group having from 1 to 6 carbon atoms, $X^1$ represents a hydrogen atom, a halogen atom, a cyano group, an alkyl group having from 1 to 6 carbon atoms or a phenyl group, A represents an aliphatic polyester chain, m is 0 or 1, and p, which may be the same or different in each branch of said macromonomer, represents an integer from 0 to 6, optionally with a polyethylene glycol derivative represented by formula (III):

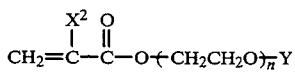

wherein $X^2$ represents a hydrogen atom, a halogen atom, a cyano group, an alkyl group having from 1 to 6 carbon atoms or a phenyl group, Y represents a hydrogen atom, an alkyl group having from 1 to 6 carbon atoms or a group represented by $-C(=O)C(X^2)=CH_2$, and n represents an integer of from 5 to 50.

2. A pharmaceutical composition of claim 1, wherein said aliphatic polyester chain represented by A is a polyester chain comprising a repeating unit represented by the formula (II):

wherein $R^2$ represents a hydrogen atom, a methyl group or an ethyl group, q is an integer of from 0 to 6, and $R^2$, q each may be the same or different in each repeating unit, and has an average polymerization degree in the range of from 5 to 500.

3. A method for controlling release of a drug comprising: placing the composition of claim 1 at a place where said drug is to be released in response to a change in temperature.

4. A method of preparing a composition that controllably releases a drug in response to a temperature change comprising: mixing the drug with the polyfunctional macromonomer represented by formula (I):

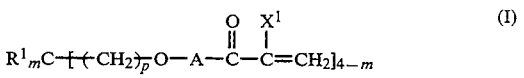

wherein $R^1$ represents a hydrogen atom or an alkyl group having from 1 to 6 carbon atoms, $X^1$ represents a hydrogen atom, a halogen atom, a cyano group, an alkyl group having from 1 to 6 carbon atoms or a phenyl group, A represents an aliphatic polyester chain, m is 0 or 1, and p, which may be the same or different in each branch of said macromonomer, represents an integer from 0 to 6, optionally with a polyethylene glycol derivative represented by formula (III):

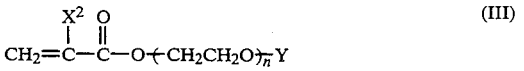

wherein $X^2$ represents a hydrogen atom, a halogen atom, a cyano group, an alkyl group having from 1 to 6 carbon atoms or a phenyl group, Y represents a hydrogen atom, an alkyl group having from 1 to 6 carbon atoms or a group represented by $-C(=O)C(X^2)=CH_2$, and n represents an integer from 5 to 50, followed by polymerization to obtain a polyester gel; or first obtaining said polyester gel and then impregnating the gel with said drug; or sealing the drug into said polyester gel having a film, membrane, tube or capsule shape.

* * * * *